(12) United States Patent
deLong et al.

(10) Patent No.: US 8,871,757 B2
(45) Date of Patent: *Oct. 28, 2014

(54) 6-AND 7-AMINO ISOQUINOLINE COMPOUNDS AND METHODS FOR MAKING AND USING THE SAME

(75) Inventors: Mitchell A. deLong, Chapel Hill, NC (US); Jill Marie Sturdivant, Chapel Hill, NC (US); Geoffrey Richard Heintzelman, Durham, NC (US); Susan M. Royalty, Cary, NC (US)

(73) Assignee: Aerie Pharmaceuticals, Inc., Research Triangle Park, NC (US)

( * ) Notice: Subject to any disclaimer, the term of this patent is extended or adjusted under 35 U.S.C. 154(b) by 118 days.

This patent is subject to a terminal disclaimer.

(21) Appl. No.: 12/704,822

(22) Filed: Feb. 12, 2010

(65) Prior Publication Data

US 2010/0144713 A1    Jun. 10, 2010

Related U.S. Application Data

(63) Continuation of application No. 12/009,326, filed on Jan. 17, 2008.

(51) Int. Cl.
*A61K 31/472* (2006.01)
*A61K 31/4725* (2006.01)
*C07D 217/02* (2006.01)
*C07D 409/12* (2006.01)

(52) U.S. Cl.
CPC ............ *C07D 217/02* (2013.01); *C07D 409/12* (2013.01)
USPC .................... 514/218; 514/235.2; 514/253.05; 514/310; 540/575; 544/128; 544/363; 546/143

(58) Field of Classification Search
None
See application file for complete search history.

(56) References Cited

U.S. PATENT DOCUMENTS

| | | | |
|---|---|---|---|
| 4,146,637 A | 3/1979 | Metz et al. | |
| 4,456,757 A | 6/1984 | Hidaka et al. | |
| 4,709,032 A | 11/1987 | Hidaka et al. | |
| 4,911,928 A | 3/1990 | Wallach | |
| 4,954,512 A | 9/1990 | Oguro et al. | |
| 5,508,288 A | 4/1996 | Forbes et al. | |
| 5,519,036 A | 5/1996 | Himmelsbach et al. | |
| 5,798,380 A | 8/1998 | Kaufman et al. | |
| 5,891,646 A | 4/1999 | Barak et al. | |
| 6,110,693 A | 8/2000 | Barak et al. | |
| 6,110,912 A | 8/2000 | Kaufman et al. | |
| 6,362,177 B1 | 3/2002 | Shiota et al. | |
| 6,586,425 B2 | 7/2003 | Kaufman et al. | |
| 6,699,891 B1 | 3/2004 | Kawanishi et al. | |
| 6,787,534 B2 | 9/2004 | Haneda et al. | |
| 7,268,143 B2 | 9/2007 | Jagtap et al. | |
| 7,329,684 B2 | 2/2008 | Mjalli et al. | |
| 7,345,158 B2 | 3/2008 | Egashira et al. | |
| 7,361,678 B2 | 4/2008 | Mjalli et al. | |
| 7,374,891 B2 | 5/2008 | Shahbaz | |
| 7,378,498 B2 | 5/2008 | Worley et al. | |
| 8,716,310 B2 | 5/2014 | deLong et al. | |
| 2004/0091946 A1 | 5/2004 | Oakley et al. | |
| 2004/0176462 A1 | 9/2004 | Kawanishi et al. | |
| 2005/0032125 A1 | 2/2005 | Oakley et al. | |
| 2005/0176712 A1 | 8/2005 | Wakabayashi et al. | |
| 2005/0282805 A1 | 12/2005 | Hangeland et al. | |
| 2006/0270670 A1 | 11/2006 | Chew et al. | |
| 2007/0111983 A1 | 5/2007 | Fong | |
| 2007/0123561 A1 | 5/2007 | Lee et al. | |
| 2007/0129404 A1 | 6/2007 | Hagihara et al. | |
| 2007/0135499 A1 | 6/2007 | deLong et al. | |
| 2007/0142429 A1 | 6/2007 | deLong et al. | |
| 2007/0149473 A1 | 6/2007 | Chatterton et al. | |
| 2007/0149548 A1 | 6/2007 | Hellberg et al. | |
| 2007/0167444 A1 | 7/2007 | Kuramochi et al. | |
| 2007/0173530 A1 | 7/2007 | deLong et al. | |
| 2007/0238741 A1 | 10/2007 | Nagarathnam et al. | |
| 2008/0021026 A1 | 1/2008 | Kahraman et al. | |
| 2008/0021217 A1 | 1/2008 | Borchardt | |
| 2008/0058384 A1 | 3/2008 | Lee et al. | |
| 2008/0096238 A1 | 4/2008 | Sharif et al. | |
| 2008/0125427 A1 | 5/2008 | Sehon et al. | |
| 2008/0139595 A1 | 6/2008 | Schirok et al. | |
| 2008/0153799 A1 | 6/2008 | Laurent et al. | |
| 2008/0153813 A1 | 6/2008 | Chen et al. | |
| 2008/0161297 A1 | 7/2008 | Bosanac et al. | |
| 2008/0167340 A1 | 7/2008 | deLong et al. | |

(Continued)

FOREIGN PATENT DOCUMENTS

EP    0232569    8/1987
EP    0389995    10/1990

(Continued)

OTHER PUBLICATIONS

STN Registry Database entry for CAS RN 309903-43-6, Published in database Dec. 20, 2000.*
Ito et al. Cancer Science 94(1), 3-8 (2003).*
United States Office Action for U.S. Appl. No. 12/639,670 dated Jul. 27, 2011 (5 pages).
European Patent Office Action for Application No. 097907752 dated Oct. 24, 2011 (5 pages).

(Continued)

*Primary Examiner* — Alicia L Otton
(74) *Attorney, Agent, or Firm* — Michael Best & Friedrich LLP

(57) ABSTRACT

6- and 7-amino isoquinoline compounds are provided that influence, inhibit or reduce the action of a kinase. Pharmaceutical compositions including therapeutically effective amounts of the 6- and 7-aminoisoquinoline compounds and pharmaceutically acceptable carriers are also provided. Various methods using the compounds and/or compositions to affect disease states or conditions such as cancer, obesity and glaucoma are also provided.

48 Claims, No Drawings

(56) References Cited

U.S. PATENT DOCUMENTS

| | | |
|---|---|---|
| 2008/0194584 A1 | 8/2008 | Birault et al. |
| 2008/0275029 A1 | 11/2008 | Berdini et al. |
| 2009/0005321 A1 | 1/2009 | Zimmer et al. |
| 2009/0069371 A1 | 3/2009 | deLong et al. |
| 2009/0186917 A1 | 7/2009 | deLong et al. |
| 2010/0022585 A1 | 1/2010 | deLong et al. |
| 2010/0093790 A1 | 4/2010 | deLong et al. |
| 2010/0105650 A1 | 4/2010 | Plettenburg et al. |
| 2010/0137364 A1 | 6/2010 | deLong et al. |
| 2010/0144713 A1 | 6/2010 | deLong et al. |
| 2010/0280011 A1 | 11/2010 | deLong et al. |
| 2011/0183965 A1 | 7/2011 | deLong et al. |
| 2011/0319390 A1 | 12/2011 | deLong et al. |
| 2012/0135984 A1 | 5/2012 | deLong et al. |
| 2012/0196916 A1 | 8/2012 | deLong et al. |
| 2013/0137721 A1 | 5/2013 | deLong et al. |
| 2014/0187617 A1 | 7/2014 | deLong et al. |

FOREIGN PATENT DOCUMENTS

| | | | |
|---|---|---|---|
| EP | 0482939 | 4/1992 | |
| EP | 1550660 | 7/2005 | |
| JP | 2005227441 | 8/2005 | |
| JP | 2007236388 | 9/2007 | |
| JP | 2007246466 | 9/2007 | |
| WO | 93/18028 | 9/1993 | |
| WO | WO 00/71508 | * 11/2000 | ............ C07C 311/16 |
| WO | 00/76970 | 12/2000 | |
| WO | 01/37826 | 5/2001 | |
| WO | WO 01/47891 | 7/2001 | |
| WO | WO 01/53268 | 7/2001 | |
| WO | WO 01/53274 | 7/2001 | |
| WO | WO 01/56607 | 8/2001 | |
| WO | WO 02/22576 | 3/2002 | |
| WO | WO 02/32864 | 4/2002 | |
| WO | 02/085857 | 10/2002 | |
| WO | 02/085859 | 10/2002 | |
| WO | WO 03/073999 | 9/2003 | |
| WO | WO 03/080578 | 10/2003 | |
| WO | 2004/029045 | 4/2004 | |
| WO | 2004/078747 | 9/2004 | |
| WO | WO 2005/020921 | 3/2005 | |
| WO | WO 2005/035503 | 4/2005 | |
| WO | WO 2005/037257 | 4/2005 | |
| WO | WO 2006/041119 | 4/2006 | |
| WO | 2006/051290 | 5/2006 | |
| WO | WO 2006/051290 | 5/2006 | |
| WO | 2006/062982 | 6/2006 | |
| WO | 2006/076706 | 7/2006 | |
| WO | WO 2007/008926 | 1/2007 | |
| WO | WO 2007/008942 | 1/2007 | |
| WO | WO 2007/060028 | 5/2007 | |
| WO | 2007/065916 | 6/2007 | |
| WO | WO 2007/065916 | 6/2007 | |
| WO | WO 2007/076360 | 7/2007 | |
| WO | WO 2007/076367 | 7/2007 | |
| WO | WO 2007/100880 | 9/2007 | |
| WO | WO 2007/142323 | 12/2007 | |
| WO | WO 2008/011557 | 1/2008 | |
| WO | WO 2008/011560 | 1/2008 | |
| WO | WO 2008/016016 | 2/2008 | |
| WO | WO 2008/036459 | 3/2008 | |
| WO | WO 2008/036540 | 3/2008 | |
| WO | WO 2008/049000 | 4/2008 | |
| WO | WO 2008/049919 | 5/2008 | |
| WO | WO 2008/054599 | 5/2008 | |
| WO | WO 2008/077057 | 6/2008 | |
| WO | WO 2008/077550 | 7/2008 | |
| WO | WO 2008/077551 | 7/2008 | |
| WO | WO 2008/077552 | 7/2008 | |
| WO | WO 2008/077553 | 7/2008 | |
| WO | WO 2008/077554 | 7/2008 | |
| WO | WO 2008/077555 | 7/2008 | |
| WO | WO 2008/077556 | 7/2008 | |
| WO | WO 2008/079880 | 7/2008 | |
| WO | WO 2008/079945 | 7/2008 | |
| WO | WO 2008/086269 | 7/2008 | |
| WO | WO 2008/124665 | * 10/2008 | ............ A01N 43/42 |
| WO | WO 2009/091898 | 7/2009 | |
| WO | WO 2010/011853 | 1/2010 | |
| WO | 2010/126626 | 11/2010 | |
| WO | 2010/127329 | 11/2010 | |
| WO | 2010/127330 | 11/2010 | |
| WO | WO 2010/126626 | 11/2010 | |
| WO | WO 2010/127329 | 11/2010 | |
| WO | WO 2010/127330 | 11/2010 | |

OTHER PUBLICATIONS

Hazeldine, S.T. et al., "II. Synthesis and biological evaluation of some bioisosteres and cogeners of the antitumour agent, 2{4[7-chloro-2-quinoxalinyl)oxy]phenoxy}propionic acid (XK469)," J. Med. Chem. (2002) 45:3130-3137.

Hu, E et al., "Rho kinase as potential therapeutic target for cardiovascular diseases: opportunities and challenges," Exp. Opin. Ther. Targets (2005) 9:715-736.

Parang, K. et al., "Design strategies for protein kinase inhibitors," Curr. Opin. In Drug Disc. & Dev. (2004) 7 (5):617-629.

International Search Report and Written Opinion for Application No. PCT/US2007/078343 dated Apr. 30, 2008 (12 pages).

Banker, G.S. et al., Modern Pharmaceutics, Marcel Dekker, Inc., New York, (1979) Chapters 9 and 10.

Bird, G.J. et al., "N-methyl as a bioisostere for the oxygen link between the aromatic rings of aryloxyphenoxypropionate herbicides," Bioorg. Med. Chem. Lett. (1997) 7:1489-1492.

Blough BE, Keverline KI, Nie Z, Navarro H, Kuhar MJ, Carroll FI (2002). "Synthesis and transporter binding properties of 3beta-[4'-(phenylalkyl, phenylalkenyl, and phenylalkynyl) phenyltropane]-2beta-carboxylic acid methyl esters: evidence of a remote phenyl binding domain on the dopamine transporter". J. Med. Chem. 45 (18): 4029-37.

C.T.F.A. Cosmetic Ingredient Handbook, "Surfactants—Emulsifying Agents", Second Edition, The Cosmetic, Toiletry, and Fragrance Association, New York, Wenninger, J.A. et al., eds. (1992) 587-592.

Calmes et al., Eur. J. Org. Chem. 2000, 2459-2466.

Capdeville, R. et al., "Glivec (STI571, IMATINIB), A Rationally Developed, Targeted Anticancer Drug", Nature Reviews Drug Discovery (2002) 1:493-502.

Chen, P. et al., "Identification of novel and potent isoquinoline aminooxazole-based IMPDH inhibitors," Bioorg. Med. Chem. Lett. (2003) 13(7):1345-1348.

Cheung, S.T. et al. Can. J. Chem. 1977, 55,906-910.

Dancey, J. et al., "Issues and Progress with Protein Kinase Inhibitors for Cancer Treatment", Nature Reviews Drug Discovery (2003) 2:296-313.

Dorwald, F.Z., Side Reactions in Organic Synthesis. A Guide to Successful Synthesis Design, Wiley-VCH, Weinheim (2005) IX of Preface and 1-15.

Dowton et al., "Influence of Liposomal Composition on Topical Delivery of Encapsulated Cyclosporin A", S.T.P. Pharma Sciences, vol. 3, pp. 404-407 (1993).

Foye, Foye's Principles of Medicinal Chemistry, 5th Edition (2002) Lippencott, Williams, Wilkins, p. 59-63.

G.E. Torres, R.R. Gainetdinov and M.G. Caron (2003). "Plasma membrane monoamine transporters: structure, regulation and function". Nat. Rev. Neurosci. 4 (1): 13-25.

Hackam, A.S. et al., "The Wnt Signaling Pathway in Retinal Degenerations", IUBMB Life (2005) 57(6):381-388.

Hazeldine, S.T. et al., "II. Synthesis and biological evaluation of some bioisosteres and cogeners of the antitumour agent, 2 {4[7-chloro-2-quinoxalinyl)oxy]phenoxy}propionic acid (XK469)," J. Med. Chem. (2002) 45:3130-3137.

He R, Kurome T, Giberson KM, Johnson KM, Kozikowski AP (2005). "Further structure-activity relationship studies of piperidine-based monoamine transporter inhibitors: effects of piperidine ring stereochemistry on potency. Identification of norepinephrine transporter selective ligands and broad-spectrum transporter inhibitors". J. Med. Chem. 48 (25): 7970-9.

(56) References Cited

OTHER PUBLICATIONS

Helal, C.J. et al., "Discovery and SAR of 2-aminothiazole inhibitors of cyclin-dependent kinase 5/p25 as a potential treatment for Alzheimer's disease," Bioorg. Med. Chem. (2004) 14(22):5521-5525.
Hu, E. et al., "Rho kinase as potential therapeutic target for cardiovascular diseases: opportunities and challenges," Exp. Opin. Ther. Targets (2005) 9:715-736.
Inouye, Y. et al., "The Absolute Configurations of TRANS-1,2-Cyclopropanedicarboxylic Acid and TRANS-2-Phenylcyclopropanecarboxylic Acid", Int'l. J. Org. Chem. (1964) 20(5):1695-1699.
Karaman, M.W. et al., "A quantitative analysis of kinase inhibitor selectivity," Nature Biotech. (2008) 26(1):127-132.
Liljebris, C. et al., "Derivatives of 17-Phenyl-18,19,20-trinorprostaglandin F2α Isopropyl Ester: Potential Antiglaucoma Agents," J. Med. Chem. (1995) 38(2):289-304.
Loge, C; Siomboing, X et al. J, of Enzy Inhib & Med Chem, 2003,18,127-128.
Matsui, T. et al., "Novel 5-HT3 antagonists. Isoquinolinones and 3-aryl-2-pyridones," J. Med. Chem. (1992) 35:3307-3319.
McCutcheon's, "Emulsifiers & Detergents", North American Edition (1994) vol. 1:236-239.
Oakley, R.H. et al. "The Cellular Distribution of Fluorescently Labeled Arrestins Provides a Robust, Sensitive and Universal Assay for Screening G Protein-Coupled Receptors," Assay and Drug Development Technologies (2002) 1(1-1):21-30.
Parang, K. et al., "Design strategies for protein kinase inhibitors," Curr. Opin. In Drug Disc. & Dev. (2004) 7(5):617-629.
Penmetsa, K.V. et al., "Development of Reversed-Phase Chiral HPLC Methods Using Mass Spectrometry Compatible Mobile Phases", J. Liquid Chroma. Rel. Tech. (2000) 23(6-10):831-839.
Penn, R.B. et al., "Pharmacological Inhibition of Protein Kinases in Intact Cells: Antagonism of Beta Adrenergic Receptor Ligand Binding by H-89 Reveals Limitations of Usefulness." J. Pharm. Exp. Ther. (1999) 288(2):428-437.
Shankar, G. et al., "Protein-kinase-specific inhibitors block Langerhans' cell migration by inhibiting interleukin-l α release", Immunology (1999) 96:230-235.
Stirewalt, D.L. et al., "The Role of FLT3 in Haematopoietic Malignancies", Nature Reviews Cancer (2003) 3:650-665.
Van Muijlwijk-Koezen et al., "A novel class of adenosine A3 receptor-ligands. 2. Structure affinity profile of a series of isoquinoline and quinazoline compounds," J. Med. Chem. (1998) 41:3994-4000.
Wallach and Philippot, "New Type of Lipid Vesicle: Novasome®", Liposome Technology, vol. 1, pp. 141-156 (1993).
Webster, F.X. et al., "Following the Course of Resolution of Carboxylic Acids by 13C NMR Spectrometry of Amine Salts" J. Org. Chem. (1982) 47(26):5225-5226.
West, A.R., "Solid state chemistry and its applications," Wiley, New York (1988) pp. 358 and 365.
Westaway, S.M. et al., "N-tetrahydroquinolinyl, N-quinolinyl and N-isoquinolinyl biaryl carboxamides as antagonists of TRPV1," Biorg. Med. Chem. Lett. (2006) 16:4533-4536.
Westra, J. et al., "p38 Mitogen-Activated Protein Kinase (MAPK) in Rheumatoid Arthritis", Mini-Reviews in Medicinal Chemistry (2006) 6(8):867-874.
United States Office Action for U.S. Appl. No. 11/485,182 dated Apr. 16, 2009 (13 pages).
United States Office Action for U.S. Appl. No. 12/274,887 dated Jun. 16, 2009 (11 pages).
United States Patent Office Action for U.S. Appl. No. 12/639,670 dated Jan. 31, 2011 (8 pages).
United States Patent Office Action for U.S. Appl. No. 12/639,670 dated Jul. 27, 2011 (5 pages).
United States Patent Office Action for U.S. Appl. No. 11/621,887 dated May 18, 2010 (8 pages).
United States Patent Office Action for U.S. Appl. No. 11/621,887 dated Oct. 29, 2010 (14 pages).
United States Patent Office Action for U.S. Appl. No. 13/017,708 dated Apr. 3, 2012 (11 pages).
United States Office Action for U.S. Appl. No. 11/621,892 dated Aug. 8, 2008 (9 pages).
United States Office Action for U.S. Appl. No. 11/621,892 dated Mar. 9, 2009 (6 pages).
United States Patent Office Action for U.S. Appl. No. 12/701,963 dated May 10, 2011 (3 pages).
United States Patent Office Action for U.S. Appl. No. 13/230,105 dated Mar. 5, 2012 (8 pages).
United States Patent Office Action for U.S. Appl. No. 12/009,326 dated Feb. 3, 2011 (8 pages).
United States Patent Office Notice of Allowance for U.S. Appl. No. 12/009,326 dated Jan. 6, 2012 (5 pages).
United States Patent Office Action for U.S. Appl. No. 12/704,822 dated Apr. 30, 2012 (34 pages).
United States Patent Office Advisory Action for U.S. Appl. No. 11/856,740 dated Feb. 10, 2011 (3 pages).
United States Patent Office Action for U.S. Appl. No. 11/856,740 dated Dec. 6, 2010 (12 pages).
United States Patent Office Action for U.S. Appl. No. 11/856,740 dated Jun. 29, 2010 (10 pages).
United States Patent Office Action for U.S. Appl. No. 12/180,259 dated Jul. 5, 2011 (11 pages).
United States Patent Office Notice of Allowance for U.S. Appl. No. 12/180,259 dated Dec. 19, 2011 (6 pages).
United States Patent Office Action for U.S. Appl. No. 12/694,965 dated May 17, 2012 (13 pages).
Partial International Search for Application No. PCT/US2009/031117 dated Apr. 16, 2009 (4 pages).
International Search Report and Written Opinion for Application No. PCT/US2006/026976 dated Feb. 15, 2007 (14 pages).
International Search Report for Application No. PCT/US2006/026947 dated Nov. 17, 2006 (4 pages).
International Preliminary Examination Report for Application No. PCT/US2006/026947 dated Jan. 24, 2008 (10 pages).
International Search Report for Application No. PCT/US08/50374 dated Oct. 28, 2008 (7 pages).
International Preliminary Report on Patentability for Application No. PCT/US08/50374 dated Jul. 14, 2009 (12 pages).
International Search Report and Written Opinion for Application No. PCT/US2009/031117 dated Sep. 24, 2009 (13 pages).
Invitation to Pay Additional Fees and Partial International Search Report for International Application No. PCT/US2009/051569 dated Oct. 15, 2009 (4 pages).
International Search Report and Written Opinion for Application No. PCT/US2009/051569 dated May 20, 2010 (11 pages).
International Search Report and Written Opinion for Application No. PCT/US2010/33316 dated Jul. 14, 2010 (10 pages).
International Search Report and Written Opinion for Application No. PCT/US2010/33317 dated Aug. 17, 2010 (10 pages).
International Search Report and Written Opinion for Application No. PCT/US2010/022246 dated Nov. 10, 2010 (7 pages).
International Search Report and Written Opinion for Application No. PCT/US2007/078343 dated Apr. 3, 2008 (12 pages).
European Patent Office Action for Application No. 09702189.3 dated Feb. 1, 2011 (5 pages).
European Patent Office Action for Application No. 09702189.3 dated Dec. 28, 2011 (5 pages).
United States Patent Office Final Rejection for U.S. Appl. No. 13/230,105 dated Jul. 9, 2012 (11 pages).
United States Patent Office Notice of Allowance for U.S. Appl. No. 13/017,708 dated Sep. 17, 2012 (8 pages).
United States Patent Office Notice of Allowance for U.S. Appl. No. 13/017,708 dated Oct. 23, 2012 (7 pages).
United States Patent Office Notice of Allowance for U.S. Appl. No. 12/694,965 dated Nov. 2, 2012 (8 pages).
United States Patent Office Notice of Allowance for U.S. Appl. No. 12/694,965 dated Nov. 19, 2012 (4 pages).
European Patent Office Action for Application No. 12007089.1 dated Nov. 23, 2012 (5 pages).
United States Patent Office Notice of Allowance for U.S. Appl. No. 13/442,263 dated Dec. 19, 2012 (13 pages).

(56) References Cited

OTHER PUBLICATIONS

Tamura, M., et al., "Development of specific Rho-kinase inhibitors and their clinical application," Biochimica et Biophysica Acta, 2005, vol. 1754, pp. 245-252.
United States Patent Office Notice of Allowability for U.S. Appl. No. 13/017,708 dated Dec. 12, 2012 (5 pages).
European Patent Office Action for Application No. 12007093.3 dated Nov. 23, 2012 (5 pages).
European Patent Office Action for Application No. 12007092.5 dated Nov. 23, 2012 (5 pages).
United States Patent Notice of Allowance for U.S. Appl. No. 11/621,887 dated Feb. 27, 2013 (8 pages).
United States Patent Notice of Allowance for U.S. Appl. No. 13/230,105 dated Mar. 19, 2013 (5 pages).
United States Patent Notice of Allowance for U.S. Appl. No. 12/009,326 dated Feb. 25, 2013 (8 pages).
United States Patent Notice of Allowance for U.S. Appl. No. 12/180,259 dated Feb. 25, 2013 (8 pages).
Pharmasolve (N-Methyl-2-Pyrrolidone) product spcification, International Specialty Products, 2000, 10 pages.
Nakanishi et al. FEBS Letters 368, (1995) 411-414.
United States Patent Office Notice of Allowance for U.S. Appl. No. 13/442,263 dated Jun. 12, 2013 (8 Pages).
United States Patent Office action for U.S. Appl. No. 13/318,457 dated Jun. 6, 2013 (12 Pages).
United States Patent Office action for U.S. Appl. No. 13/768,594 dated Jul. 10, 2013 (14 Pages).
United States Patent Office Action for U.S. Appl. No. 13/723,811 dated Jan. 27, 2014 (8 pages).
United States Patent Office Final Rejection for U.S. Appl. No. 13/442,263 dated Dec. 6, 2013 (8 pages).
Canadian Patent Office Action for Application No. 2,712,443 dated Dec. 27, 2013 (3 pages).
Australian Patent Examination Report No. 1 for Application No. 2009206075 dated Jan. 29, 2013 (3 pages).
United States Patent Office Final Rejection for U.S. Appl. No. 13/318,457 dated Nov. 27, 2013 (13 pages).
United States Patent Office Notice of Allowance for U.S. Appl. No. 13/768,594 dated Oct. 29, 2013 (7 pages).
Japanese Patent Office Action for Application No. 2010-543237 dated Jan. 8, 2014 (2 pages—Including English Translation).
Jacobs, M. et al., "The structure of dimeric ROCK I reveals the mechanism for ligand selectivity," J. Bio. Chem., 2006, pp. 260-268, published on Jan. 6, 2006.
Meanwell, "Synopsis of some recent tactical application of bioisosteres in drug design," J. Med. Chem., 2011, vol. 54, pp. 2529-2591.
United States Patent Office Action for U.S. Appl. No. 11/856,740 dated Aug. 16, 2013 (14 pages).
European Patent Office Action for Application No. 12007093.3 dated Aug. 23, 2013 (5 pages).
Japanese Patent Office Action for Application No. 2010-543237 dated Aug. 8, 2013 (10 pages—Including English Translation).
United States Patent Office Notice of Allowance for U.S. Appl. No. 13/442,263 dated Apr. 15, 2014 (8 pages).
United States Patent Office Notice of Allowance for U.S. Appl. No. 11/856,740 dated Apr. 1, 2014 (8 pages).
European Patent Office Action for Application No. 12007093.3 dated Mar. 26, 2014 (4 pages).
United States Patent Office Action for U.S. Appl. No. 13/723,811 dated Jun. 17, 2014 (6 pages).
United States Patent Office Notice of Allowance for U.S. Appl. No. 13/723,811 dated Aug. 19, 2014 (11 pages).
United States Patent Office Action for U.S. Appl. No. 14/138,592 dated Jul. 28, 2014 (17 pages).
United States Patent Office Action for U.S. Appl. No. 14/273,895 dated Aug. 20, 2014 (8 pages).

* cited by examiner

6-AND 7-AMINO ISOQUINOLINE COMPOUNDS AND METHODS FOR MAKING AND USING THE SAME

FIELD OF THE INVENTION

The present invention relates to 6- and 7-aminoisoquinoline compounds that affect the function of kinases in a cell and that are useful as therapeutic agents or with therapeutic agents. In particular, these compounds are useful in the treatment of eye diseases such as glaucoma and for diseases characterized by abnormal growth, such as cancers.

BACKGROUND

A variety of hormones, neurotransmitters and biologically active substances control, regulate or adjust the functions of living bodies via specific receptors located in cell membranes. Many of these receptors mediate the transmission of intracellular signals by activating guanine nucleotide-binding proteins (G proteins) to which the receptor is coupled. Such receptors are generically referred to as G-protein coupled receptors (GPCRs) and include, among others, α-adrenergic receptors, β-adrenergic receptors, opioid receptors, cannabinoid receptors and prostaglandin receptors. The biological effects of activating these receptors is not direct but is mediated by a host of intracellular proteins. The importance of these secondary, or "downstream" proteins is only now being recognized and investigated as potential intervention points in disease states. One of the most important classes of these downstream effectors is the "kinase" class.

The various kinases thus play important roles in the regulation of various physiological functions. For example, kinases have been implicated in a number of disease states, including, but not limited to: cardiac indications such as angina pectoris, essential hypertension, myocardial infarction, and supraventricular and ventricular arrhythmias; congestive heart failure; atherosclerosis; renal failure, diabetes; respiratory indications such as asthma, chronic bronchitis, bronchospasm, emphysema, airway obstruction, and upper respiratory indications such as rhinitis, seasonal allergies, and inflammatory disease; inflammation in response to injury; and rheumatoid arthritis. The importance of p38 MAPK inhibitors in particular as new drugs for rheumatoid arthritis is reflected by the large number of compounds that have been developed over the last years (J. Westra and P. C. Limburg Mini-Reviews in Medicinal Chemistry Volume 6, Number 8, August 2006). Other conditions include chronic inflammatory bowel disease, glaucoma, hypergastrinemia, gastrointestinal indications such as acid/peptic disorder, erosive esophagitis, gastrointestinal hypersecretion, mastocytosis, gastrointestinal reflux, peptic ulcer, Zollinger-Ellison syndrome, pain, obesity, bulimia nervosa, depression, obsessive-compulsive disorder, organ malformations (for example, cardiac malformations), neurodegenerative diseases such as Parkinson's Disease and Alzheimer's Disease, multiple sclerosis, Epstein-Barr infection and cancer (Nature Reviews Drug Discovery 1, 493-502 2002). In other disease states, the role of kinases is only now becoming clear. The retina is a complex tissue composed of multiple interconnected cell layers, highly specialized for transforming light and color into electrical signals that are perceived by the brain. Damage or death of the primary light-sensing cells, the photoreceptors, results in devastating effects on vision. Despite the identification of numerous mutations that cause inherited retinal degenerations, the cellular and molecular mechanisms leading from the primary mutations to photoreceptor apoptosis are not well understood, but may involve the wnt pathway (A. S. Hackam, The Wnt Signaling Pathway in Retinal Degeneration IUBMB Life Volume 57, Number 6, June 2005).

The success of the tyrosine-kinase inhibitor STI571 (Gleevec) in the treatment of chronic myelogenous leukemia (Nature Reviews Drug Discovery 2, 296-313 2003) has spurred considerable efforts to develop other kinase inhibitors for the treatment of a wide range of other cancers (Nature Reviews Cancer 3, 650-665 2003). The balance between the initiation and the inactivation of intracellular signals determines the intensity and duration of the response of the receptors to stimuli such as agonists. When desensitization occurs, the mediation or regulation of the physiological function mediated or regulated by the G proteins to which the receptors are coupled is reduced or prevented. For example, when agonists are administered to treat a disease or condition by activation of certain receptors, the receptors relatively quickly become desensitized from the action of the G-protein coupled receptor kinases (GRKs) such that agonist administration may no longer result in therapeutic activation of the appropriate receptors. At that point, administration of the agonist no longer enables sufficient or effective control of or influence on the disease or condition intended to be treated.

In view of the role that kinases have in many disease states, there is an urgent and continuing need for small molecule ligands which inhibit or modulate the activity of kinases. Without wishing to be bound by theory, it is thought that modulation of the activity of kinases by the compounds of the present invention is responsible for their beneficial effects.

SUMMARY

In one aspect, the invention provides novel 6- and 7-aminoisoquinoline compounds.

In another aspect, the invention provides novel pharmaceutical compositions comprising 6- and 7-aminoisoquinolines.

In a further aspect, the invention provides methods of treating diseases comprising administering safe and effective amounts of 6- or 7-isoquinoline derivatives. Examples of suitable diseases include eye disorders such as glaucoma or a neurodegenerative eye disease.

In yet another aspect, the invention provides a method for influencing the action of a kinase in a cell, a tissue, or a living mammal comprising administering to or contacting with a cell, a tissue, or a mammal a therapeutically effective amount of a first therapeutic agent comprising at least one of a 6- or 7-aminoisoquinoline Other aspects of the invention will become apparent by consideration of the detailed description and accompanying drawings.

DETAILED DESCRIPTION

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items.

It also is understood that any numerical range recited herein includes all values from the lower value to the upper value. For example, if a concentration range is stated as 1% to 50%, it is intended that values such as 2% to 40%, 10% to 30%, or 1% to 3%, etc., are expressly enumerated in this specification. These are only examples of what is specifically intended, and all possible combinations of numerical values between and including the lowest value and the highest value enumerated are to be considered to be expressly stated in this application.

All percentages, ratios, and proportions used herein are percent by weight unless otherwise specified.

DEFINITIONS

The following is a list of definitions and abbreviations for terms, as used herein.

"AcOH" is the abbreviation for acetic acid.

"Alkyl" refers to a saturated aliphatic hydrocarbon including straight chain and branched chain groups. "Alkyl" may be exemplified by groups such as methyl, ethyl, n-propyl, isopropyl, n-butyl and the like. Alkyl groups may be substituted or unsubstituted. Substituents may also be themselves substituted. When substituted, the substituent group is preferably, but not limited to, $C_1$-$C_4$ alkyl, aryl, amino, cyano, halogen, alkoxy or hydroxyl. "$C_n$-$C_m$ alkyl" refers to alkyl groups containing n to m carbon atoms, wherein n and m are integers. In some suitable embodiments, n is about 1 member atom and m is about 5 member atoms.

"Alkenyl" refers to an unsaturated aliphatic hydrocarbon moiety including straight chain and branched chain groups. Alkenyl moieties contain at least one alkene. "Alkenyl" may be exemplified by groups such as ethenyl, n-propenyl, isopropenyl, n-butenyl and the like. Alkenyl groups may be substituted or unsubstituted. Substituents may also be themselves substituted. When substituted, the substituent group is preferably alkyl, halogen or alkoxy. Substitutients may also be themselves substituted. Substituents may be located on the alkene itself and also on the adjacent member atoms of the alkynyl moiety. "$C_n$-$C_m$ alkenyl" refers to alkenyl groups containing n to m carbon atoms, where n and m are integers. In some suitable embodiments, n is about 2 member atoms and m is about 6 member atoms.

"Alkynyl" refers to an unsaturated aliphatic hydrocarbon moiety including straight chain and branched chain groups. Alkynyl moieties contain at least one alkyne. "Alkynyl" may be exemplified by groups such as ethynyl, propynyl, n-butynyl and the like. Alkynyl groups may be substituted or unsubstituted. When substituted, the substituent group is preferably alkyl, amino, cyano, halogen, alkoxyl or hydroxyl. Substituents may also be themselves substituted. Substituents are not on the alkyne itself but on the adjacent member atoms of the alkynyl moiety. "$C_n$-$C_m$ alkynyl" refers to alkynyl groups containing n to m carbon atoms, where n and m are integers. In some suitable embodiments, n is about 2 member atoms and m is about 6 member atoms.

"Acyl" or "carbonyl" refers to the group —C(O)R wherein R is H, alkyl, alkenyl, alkynyl, aryl, heteroaryl, carbocyclic, heterocarbocyclic, $C_1$-$C_4$ alkyl aryl or $C_1$-$C_4$ alkyl heteroaryl. $C_n$-$C_m$ alkyl carbonyl refers to a group wherein the carbonyl moiety is preceded by an alkyl chain of n to m carbon atoms, where n and m are integers. In some suitable embodiments, n is about 2 member atoms and m is about 6 member atoms.

"Administering" as used herein refers to administration of the compounds as needed to achieve a desired effect.

"Alkoxy" refers to the group —O—R wherein R is acyl, alkyl alkenyl, alkyl alkynyl, aryl, carbocyclic, heterocarbocyclic, heteroaryl, $C_1$-$C_4$ alkyl aryl or $C_1$-$C_4$ alkyl heteroaryl.

"Amino" refers to the group —NR'R" wherein R' and R" are each, independently, hydrogen, alkyl, aryl, heteroaryl, $C_1$-$C_4$ alkyl aryl or $C_1$-$C_4$ alkyl heteroaryl. The R' and R" groups may themselves be linked to form a ring.

"Aryl" refers to an aromatic carbocyclic group. "Aryl" may be exemplified by phenyl. The aryl group may be substituted or unsubstituted. Substituents may also be themselves substituted. When substituted, the substituent group is preferably, but not limited to, alkyl, alkoxy, heteroaryl, acyl, carboxyl, carbonylamino, nitro, amino, cyano, halogen or hydroxyl. The substituents may be positioned at various locations on an aryl group. For example, substituents on a phenyl group may be located at an ortho-position, a meta-position, the para-position, or combinations thereof.

"$Boc_2O$" is the abbreviation for di-tert-butyl-dicarbonate.

"Carboxyl" refers to the group —C(═O)OR, where R is a $C_1$-$C_4$ alkyl.

"Carbonyl" refers to the group —C(O)R wherein each R is, independently, hydrogen, alkyl, aryl, cycloalkyl, heterocycloalkyl, heteroaryl, $C_1$-$C_4$ alkyl aryl or $C_1$-$C_4$ alkyl heteroaryl.

"Carbonylamino" refers to the group —C(O)NR'R" wherein R' and R" are, independently, hydrogen, alkyl, aryl, cycloalkyl, heterocycloalkyl, heteroaryl, $C_1$-$C_4$ alkyl aryl or $C_1$-$C_4$ alkyl heteroaryl. The R' and R" groups may themselves be linked to form a ring.

"$C_1$-$C_4$ alkyl aryl" refers to $C_1$-$C_4$ alkyl groups having an aryl substituent such that the aryl substituent is bonded through an alkyl group. "$C_1$-$C_4$ alkyl aryl" may be exemplified by benzyl.

"$C_1$-$C_4$ alkyl heteroaryl" refers to $C_1$-$C_4$ alkyl groups having a heteroaryl substituent such that the heteroaryl substituent is bonded through an alkyl group.

"Carbocyclic group" or "cycloalkyl" means a monovalent saturated or unsaturated hydrocarbon ring. Carbocyclic groups are monocyclic, or are fused, spiro, or bridged bicyclic ring systems. Monocyclic carbocyclic groups contain 3 to 10 carbon atoms, preferably 4 to 7 carbon atoms, and more preferably 5 to 6 carbon atoms in the ring. Bicyclic carbocyclic groups contain 8 to 12 carbon atoms, preferably 9 to 10 carbon atoms in the ring. Carbocyclic groups may be substituted or unsubstituted. Suitable substituents include, but are not limited to, lower alkyl, hydroxyl, nitrile, halogen and amino. Substituents may also be themselves substituted. Preferred carbocyclic groups include cyclopropyl, cyclobutyl, cyclopentyl, cyclohexyl, cyclohexenyl, and cycloheptyl. More preferred carbocyclic groups include cyclopropyl and cyclobutyl. The most preferred carbocyclic group is cyclopropyl. Carbocyclic groups are not aromatic.

"Controlling the disease or condition" means changing the activity of one or more kinases to affect the disease or condition.

"Disease or condition associated with kinase activity" means a disease or condition treatable, in whole or in part, by inhibition of one or more kinases.

"DMAP" is the abbreviation for dimethyl aminopyridine.

"DMF" is the abbreviation for dimethylformamide.

"DMSO" is the abbreviation for dimethyl sulfoxide.

"DMS" is the abbreviation for dimethyl sulfate.

"EDC" is the abbreviation for N-(3-dimethylaminopropyl)-N'-ethylcarbodiimide hydrochloride.

"Excipient" refers to physiologically compatible additives useful in preparation of a pharmaceutical composition. Examples of pharmaceutically acceptable carriers and excipients can, for example, be found in Remington Pharmaceutical Science, 16$^{th}$ Ed.

"Eye disease" as used herein includes, but is not limited to, glaucoma, allergy, cancers of the eye, neurodegenerative diseases of the eye, and dry eye.

"FBS" is the abbreviation for fetal bovine serum.

"Halogen" refers to fluoro, chloro, bromo or iodo moieties. Preferably, the halogen is fluoro, chloro, or bromo.

"HATU" is the abbreviation for 2-(7-Aza-1H-benzotriazole-1-yl)-1,1,3,3-tetramethyluronium hexafluorophosphate.

"Heteroaryl" or "heteroaromatic" refers to a monocyclic or bicyclic aromatic carbocyclic radical having one or more heteroatoms in the carbocyclic ring. Heteroaryl may be substituted or unsubstituted. When substituted, the substituents may themselves be substituted. Preferred, but non-limiting substituents, are aryl, $C_1$-$C_4$ alkyl aryl, amino, halogen, hydroxy, cyano, nitro, carboxyl, carbonylamino or $C_1$-$C_4$ alkyl. Preferred heteroaromatic groups include tetrazoyl, triazolyl, thienyl, thiophenyl, thiazolyl, purinyl, pyrimidyl, pyridyl, and furanyl. More preferred heteroaromatic groups include benzothiofuranyl, thiophenyl, thienyl, furanyl, tetrazoyl, triazolyl, and pyridyl.

"Heteroatom" means an atom other than carbon in the ring of a heterocyclic group or a heteroaromatic group or the chain of a heterogeneous group. Preferably, heteroatoms are selected from the group consisting of nitrogen, sulfur, and oxygen atoms. Groups containing more than one heteroatom may contain different heteroatoms.

"Heterocarbocyclic group" or "heterocycloalkyl" or "heterocyclic" means a monovalent saturated or unsaturated hydrocarbon ring containing at least one heteroatom. Heterocarbocyclic groups are monocyclic, or are fused, Spiro, or bridged bicyclic ring systems. Monocyclic heterocarbocyclic groups contain 3 to 10 carbon atoms, preferably 4 to 7 carbon atoms, and more preferably 5 to 6 carbon atoms in the ring. Bicyclic heterocarbocyclic groups contain 8 to 12 carbon atoms, preferably 9 to 10 carbon atoms in the ring. Heterocarbocyclic groups may be substituted or unsubstituted. Suitable substituents include, but are not limited to, lower alkyl, hydroxyl, nitrile, halogen and amino. Substituents may also be themselves substituted. Preferred heterocarbocyclic groups include epoxy, tetrahydrofuranyl, azacyclopentyl, azacyclohexyl, piperidyl, and homopiperidyl. More preferred heterocarbocyclic groups include piperidyl, and homopiperidyl. The most preferred heterocarbocyclic group is piperidyl. Heterocarbocyclic groups are not aromatic.

"Hydroxy" or "hydroxyl" means a chemical entity that consists of —OH. Alcohols contain hydroxy groups. Hydroxy groups may be free or protected. An alternative name for hydroxyl is hydroxy "LDA" is the abbreviation for lithium diisopropyl amide.

"Linker" means a linear chain of n member atoms where n is an integer from 1 to 4.

"Member atom" means a carbon, nitrogen, oxygen or sulfur atom. Member atoms may be substituted up to their normal valence.

"Pharmaceutically acceptable carrier" means a carrier that is useful for the preparation of a pharmaceutical composition that is generally compatible with the other ingredients of the composition, not deleterious to the recipient, and neither biologically nor otherwise undesirable. "A pharmaceutically acceptable carrier" includes one or more than one carrier. Embodiments include carriers for topical, ocular, parenteral, intravenous, intraperitoneal intramuscular, sublingual, nasal and oral administration. "Pharmaceutically acceptable carrier" also includes agents for preparation of aqueous dispersions and sterile powders for injection or dispersions.

"Ring" means a collection of member atoms that are cyclic. Rings may be carbocyclic, aromatic, or heterocyclic or heteroaromatic, and may be substituted or unsubstituted, and may be saturated or unsaturated. Ring junctions with the main chain may be fused or spirocyclic. Rings may be monocyclic or bicyclic. Rings contain at least 3 member atoms and at most 12 member atoms. Monocyclic rings may contain 3 to 10 member atoms and bicyclic rings may contain from 8 to 12 member atoms. Bicyclic rings themselves may be fused or spirocyclic. Rings may be substituted or unsubstituted. Suitable substituents include, but are not limited to, lower alkyl, hydroxyl, nitrile, halogen and amino.

"Sulfonyl" refers to the —S(O)$_2$R' group wherein R' is alkoxy, alkyl, aryl, carbocyclic, heterocarbocyclic, heteroaryl, $C_1$-$C_4$ alkyl aryl or $C_1$-$C_4$ alkyl heteroaryl.

"Sulfonylamino" refers to the —S(O)$_2$NR'R" group wherein R' and R" are, independently, alkyl, aryl, heteroaryl, $C_1$-$C_4$ alkyl aryl or $C_1$-$C_4$ alkyl heteroaryl.

"Therapeutically effective amount" refers to a dosage of the compounds or compositions effective for influencing, reducing or inhibiting the activity of or preventing activation of a kinase. This term as used herein may also refer to an amount effective at bringing about a desired in vivo effect in an animal, preferably, a human, such as reduction in intraocular pressure.

"THF" is the abbreviation for tetrahydrofuran.

"Thioalkyl" refers to the group —S-alkyl.

6- and 7-Aminoisoquinoline Compounds

Novel 6- and 7-aminoisoquinoline compounds and methods of using those compounds to treat disease are provided.

The 6-aminoisoquinoline compounds may be represented by Formula (I):

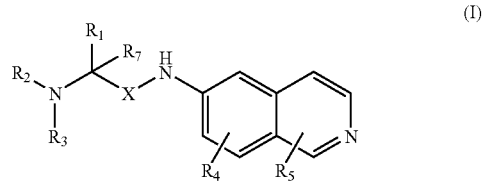

(I)

any optical isomer, diastereomer, or enantiomer of Formula I or a physiologically acceptable salt or solvate thereof, wherein $R_1$ is an aryl group, a heteroaryl group, a cycloalkyl group, a heterocycloalkyl group, the stereocenter being either 'R' or 'S' in configuration, $R_7$ is hydrogen, $C_1$-$C_4$ alkyl, cyano, or $R_1$ and $R_7$ combine to form a ring of at least three and at most eight member atoms, $R_2$, and $R_3$ are, independently, hydrogen, hydroxyl, halogen, $C_1$-$C_4$ alkyl, $C_2$-$C_4$ alkenyl, $C_2$-$C_4$ alkynyl, amino, nitro, cyano, $C_1$-$C_4$ carbonyl, $C_1$-$C_4$ carbonylamino, $C_1$-$C_4$ alkoxy, $C_1$-$C_4$ sulfonyl, $C_1$-$C_4$ sulfonylamino, $C_1$-$C_4$ thioalkyl $C_1$-$C_4$ carboxyl, cycloalkyl, heterocycloalkyl, aryl, $C_1$-$C_4$ alkyl aryl, heteroaryl, or $C_1$-$C_4$ alkyl heteroaryl; or $R_2$ and $R_3$ combine to form a ring of at least five and at most eight member atoms, X is a carbonyl group, a sulfone group, thiocarbonyl or alkylene, and $R_4$ and $R_5$ are independently, halogen, hydrogen, hydroxy, alkyl, alkoxy, amino, carbonyl, cycloalkyl, heterocycloalkyl, aryl, $C_1$-$C_4$ alkyl aryl, heteroaryl, $C_1$-$C_4$ alkyl heteroaryl, alkenyl, alkynyl, nitro, cyano, $C_1$-$C_4$ carbonylamino, $C_1$-$C_4$ sulfonyl, $C_1$-$C_4$ sulfonylamino, $C_1$-$C_4$ thioalkyl or $C_1$-$C_4$ carboxyl.

In a preferred embodiment of Formula (I), X is a carbonyl group, $R_1$ is an aryl group, $R_4$ is hydrogen and $R_5$ is hydrogen. In another preferred embodiment of Formula (I), X is a carbonyl group, $R_1$ is a cycloalkyl group, $R_2$ is a methyl group, $R_3$ is a methyl group, and $R_5$ is a hydroxyl group.

In other preferred embodiments of Formula I, X is a carbonyl group, $R_4$ is hydrogen, $R_5$ is hydrogen, and $R_7$ contains 1 (one) member atoms. In further preferred embodiments, X is a carbonyl group, and $R_1$ is a para-substituted aryl group. In some preferred embodiments, X is a carbonyl group, and $R_2$ is a lower alkyl group such as a $C_1$-$C_4$ alkyl group.

In yet other preferred embodiments of Formula I, X is a sulfone group, $R_4$ is hydrogen, $R_5$ is hydrogen, and $R_7$ contains 1 (one) member atom. In further preferred embodiments, X is a sulfone group, and $R_1$ is a para-substituted aryl group. In some preferred embodiments X is a sulfone group, and $R_2$ is a lower alkyl group such as a $C_1$-$C_4$ alkyl group. In other preferred embodiments, X is a sulfone group, and $R_2$ and $R_3$ combine to form a ring of at least five and at most eight member atoms.

The 7-aminoisoquinoline compounds may be represented by Formula (II)

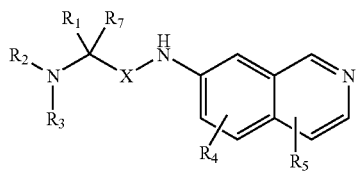

any optical isomer, diastereomer, or enantiomer of Formula II or a physiologically acceptable salt or solvate thereof, wherein $R_1$ is hydrogen, a lower alkyl group, an aryl group, a heteroaryl group, a cycloalkyl group, a heterocycloalkyl group, the stereocenter being either 'R' or 'S' in configuration, $R_7$ is $C_1$-$C_6$ alkyl, $C_2$-$C_6$ alkenyl, $C_2$-$C_6$ alkynyl, cyano, aryl group, heteroaryl group, alkyl aryl group, cycloalkyl group, heterocycloalkyl group or $R_1$ and $R_7$ combine to form a ring, of at least three and at most 8 member atoms, $R_2$, and $R_3$ are, independently, hydrogen, hydroxyl, halogen, $C_1$-$C_4$ alkyl, $C_2$-$C_4$ alkenyl, $C_2$-$C_4$ alkynyl, amino, nitro, cyano, $C_1$-$C_4$ carbonyl, $C_1$-$C_4$ carbonylamino, $C_1$-$C_4$ alkoxy, $C_1$-$C_4$ sulfonyl, $C_1$-$C_4$ sulfonylamino, $C_1$-$C_4$ thioalkyl or $C_1$-$C_4$ carboxyl, aryl group, heteroaryl group, alkyl aryl group, cycloalkyl group or heterocycloalkyl group; or $R_2$ and $R_3$ combine to form a ring of at least five and at most 8 member atoms, X is a carbonyl group, sulfone group, thiocarbonyl or alkylene, and $R_4$ and $R_5$ are independently, halogen, hydrogen, hydroxy, alkyl, alkoxy, amino, carbonyl, cycloalkyl, heterocycloalkyl, aryl, $C_1$-$C_4$ alkyl aryl, heteroaryl, $C_1$-$C_4$ alkyl heteroaryl.

The 6- or 7-aminoisoquinoline compounds may be synthesized by the general schemes set forth below.

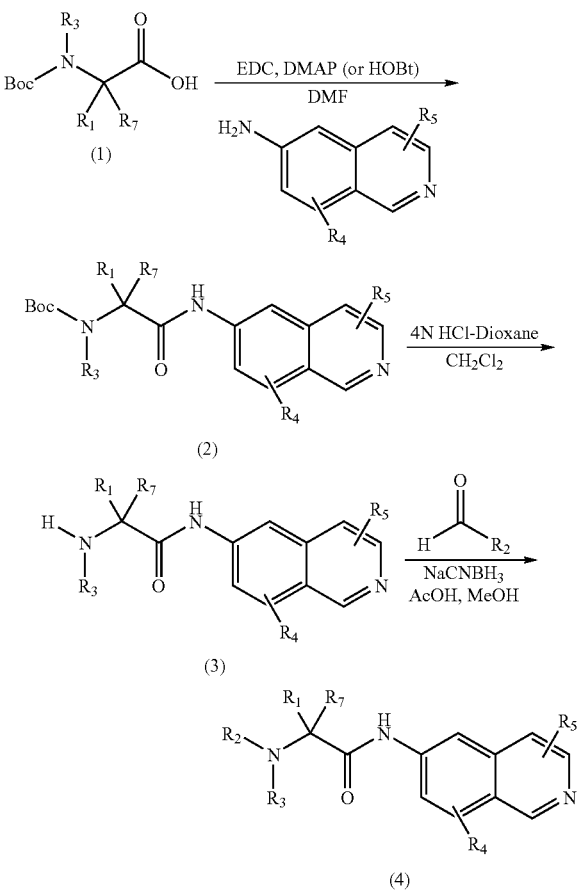

where $R_1$, $R_2$, $R_3$, $R_4$, $R_5$, $R_7$ and X are defined above.

Scheme One:

The selected acid (1) was activated with an appropriate agent such as N-(3-dimethylaminopropyl)-N'-ethylcarbodiimide hydrochloride ("EDC") then coupled to 6- or 7-aminoisoquinoline using standard coupling procedures to form the desired intermediate (2). The amine (2) was reacted with the HCl in methylene chloride to generate the amide (3) directly. When an $R_2$ group was desired to be added, (3) was subjected to reductive amination conditions to generate the N,N-disubstituted compounds of type (4).

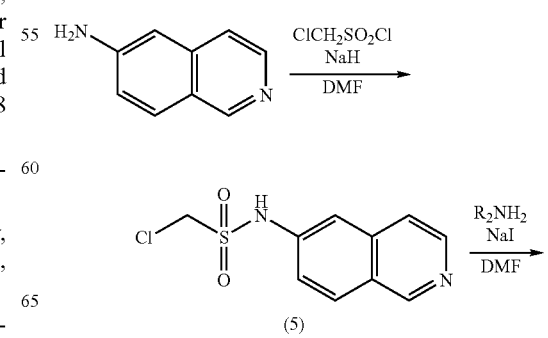

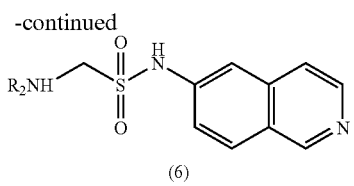

(6)

Scheme Two:

6-Aminoisoquinoline is treated with sodium hydride and then chloromethanesulfonyl chloride to provide the sulfonamide 5. Treatment of the chlorosulfonamide 5 with an amine in the presence of sodium iodide provides the desired amine 6.

Using reactions similar to those in Scheme Two, compounds with a cycloalkyl moiety can be prepared. The compounds are obtained by using a cycloalkylamine instead of an aniline to displace the chloride (Scheme Three).

Scheme Three

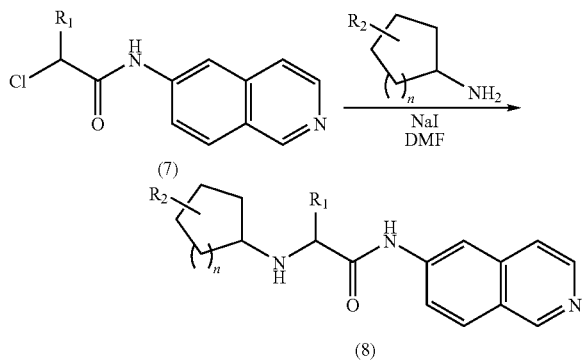

Scheme Three:

Treatment of the chloroamide 7 with an amine in the presence of sodium iodide provides the desired product 8.

Methods

One embodiment of the invention includes a method of treating a condition comprising administering to a subject in need of treatment a safe and effective amount of a 6- or 7-aminoisoquinoline derivative, wherein the condition is selected from the group consisting of eye disease (e.g., retinal degradation or glaucoma), bone disorder, obesity, heart disease, hepatic disease, renal disease, pancreatitis, cancer, myocardial infarct, gastric disturbance, hypertension, fertility control, disorders of hair growth, nasal congestion, neurogenic bladder disorder, gastrointestinal disorder, and dermatological disorder.

The 6- or 7-aminoisoquinoline compounds of the above Formulae and compositions including them have kinase inhibitory activity and are thus useful in influencing or inhibiting the action of kinases, and in treatment and/or prevention of diseases or conditions influenced by kinases. The 6- or 7-aminoisoquinolines may be used to influence or inhibit the action of kinases either in a cell in vitro or in a cell in a living body in vivo. Specifically, in one embodiment, a method is provided of inhibiting the action of a kinase comprising applying to a medium such as an assay medium or contacting with a cell either in a cell in vitro or in a cell in a living body in vivo an effective inhibitory amount of a compound according to Formulae (I) or (II). Exemplary kinases that may be influenced include, but are not limited to, ROK-I, ROK-II, PKA, PKC, CAM Kinases, GRK-2, GRK-3, GRK-5 or GRK-6. In a preferred embodiment, the kinase inhibited is a rho kinase. In another embodiment, the 6- or 7-aminoisoquinolines according to Formulae (I) or (II) are used in methods for influencing (e.g. inhibiting or reducing) the action of a kinase in a cell comprising administering to, or contacting with, the cell an effective amount of one or more 6- or 7-aminoisoquinolines for influencing the action of the kinase in the cell. The one or more of the 6- or 7-aminoisoquinolines are preferably administered in a pharmaceutically acceptable formulation, such as in or with a pharmaceutically acceptable carrier, when the 6- or 7-aminoisoquinolines are administered to a cell or cells in a living organism or body.

Treatment or prevention of diseases or conditions for which the 6- or 7-aminoisoquinolines may be useful includes any of the diseases or conditions associated with kinase activity or diseases or conditions affected by kinases. Examples of these types of diseases include retinal degradation, glaucoma and cancer.

The 6- or 7-aminoisoquinolines in some embodiments will be administered in conjunction with the administration of a second or in some cases a third therapeutic agent which is directed to the treatment or prevention of a condition or disease affected by those specific kinases. Combining administration of the 6- or 7-aminoisoquinolines with other therapeutic agents will provide a reduction or prevention of the condition or disease to which the therapeutic agent is directed, resulting in improving the ability of the therapeutic agent to have the desired effect over a longer period of time. Additionally, the administration of the therapeutic agent or receptor agonist with a 6- or 7-aminoisoquinoline formulation will enable lower doses of the other therapeutic agents to be administered for a longer period of time. The therapeutic agents and/or the 6- or 7-aminoisoquinoline compounds are preferably administered in a pharmaceutically acceptable formulation with a pharmaceutically acceptable carrier when the 6- or 7-aminoisoquinolines are administered to a cell or cells in a living organism or a mammal, preferably human.

Compositions

In another embodiment of the invention, a pharmaceutical composition is provided, comprising:

a) a 6-aminoisoquinoline derivative according to Formula I

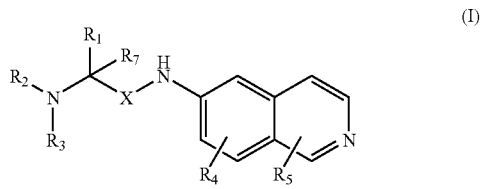

(I)

any optical isomer, diastereomer, or enantiomer of Formula I or a physiologically acceptable salt or solvate thereof, wherein $R_1$ is an aryl group, a heteroaryl group, a cycloalkyl group, a heterocycloalkyl group, the stereocenter being either 'R' or 'S' in configuration, $R_7$ is hydrogen, $C_1$-$C_4$ alkyl, cyano, or $R_1$ and $R_7$ combine to form a ring of at least three and at most eight member atoms, $R_2$, and $R_3$ are, independently, hydrogen, hydroxyl, halogen, $C_1$-$C_4$ alkyl, $C_2$-$C_4$ alkenyl, $C_2$-$C_4$ alkynyl, amino, nitro, cyano, $C_1$-$C_4$ carbonyl, $C_1$-$C_4$ carbonylamino, $C_1$-$C_4$ alkoxy, $C_1$-$C_4$ sulfonyl, $C_1$-$C_4$ sulfonylamino, $C_1$-$C_4$ thioalkyl or $C_1$-$C_4$ carboxyl, cycloalkyl, heterocycloalkyl, aryl, $C_1$-$C_4$ alkyl aryl, heteroaryl, or $C_1$-$C_4$ alkyl heteroaryl; or $R_2$ and $R_3$ combine to form a ring of at least five and at most eight member atoms, X is a carbonyl group, a sulfone group, a thiocarbonyl, methylene, and $R_4$ and $R_5$ are independently, halogen, hydrogen, hydroxy, alkyl, alkoxy, amino, carbonyl, cycloalkyl, heterocycloalkyl, aryl, $C_1$-$C_4$ alkyl aryl, heteroaryl, $C_1$-$C_4$ alkyl heteroaryl, alkenyl, alkynyl, nitro, cyano, $C_1$-$C_4$ carbonylamino, $C_1$-$C_4$ sulfonyl, $C_1$-$C_4$ sulfonylamino, $C_1$-$C_4$ thioalkyl or $C_1$-$C_4$ carboxyl, or a 7-isoquinoline derivative according to Formula II

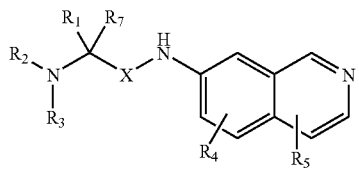

any optical isomer, diastereomer, or enantiomer of Formula IV or a physiologically acceptable salt or solvate thereof, wherein $R_1$ is hydrogen, a lower alkyl group, an aryl group, a heteroaryl group, a cycloalkyl group, a heterocycloalkyl group, the stereocenter being either 'R' or 'S' in configuration, $R_7$ is $C_1$-$C_6$ alkyl, $C_2$-$C_6$ alkenyl, $C_2$-$C_6$ alkynyl, cyano, aryl group, heteroaryl group, alkyl aryl group, cycloalkyl group, heterocycloalkyl group or $R_1$ and $R_7$ combine to form a ring, of at least three and at most 8 member atoms, $R_2$, and $R_3$ are, independently, hydrogen, hydroxyl, halogen, $C_1$-$C_4$ alkyl, $C_2$-$C_4$ alkenyl, $C_2$-$C_4$ alkynyl, amino, nitro, cyano, $C_1$-$C_4$ carbonyl, $C_1$-$C_4$ carbonylamino, $C_1$-$C_4$ alkoxy, $C_1$-$C_4$ sulfonyl, $C_1$-$C_4$ sulfonylamino, $C_1$-$C_4$ thioalkyl or $C_1$-$C_4$ carboxyl, aryl group, heteroaryl group, alkyl aryl group, cycloalkyl group or heterocycloalkyl group; or $R_2$ and $R_3$ combine to form a ring of at least five and at most 8 member atoms, X is a carbonyl group, sulfone group, thiocarbonyl or methylene, and $R_4$ and $R_5$ are independently, halogen, hydrogen, hydroxy, alkyl, alkoxy, amino, carbonyl, cycloalkyl, heterocycloalkyl, aryl, $C_1$-$C_4$ alkyl aryl, heteroaryl, $C_1$-$C_4$ alkyl heteroaryl, and b) a carrier.

Compositions including the 6-aminoisoquinolines of Formula (I) or the 7-aminoisoquinolines of Formula (II) may be obtained in the form of various salts or solvates. As the salts, physiologically acceptable salts or salts available as raw materials are used.

Compositions may include one or more of the isoforms, optical isomers, diasteriomer, or enantiomers of Formula (I) when present. When racemates exists, each enantiomer may be separately used, or they may be combined in any proportion.

Pharmaceutical compositions for use in accordance with the present invention may be formulated in a conventional manner using one or more physiologically acceptable carriers or excipients. Thus, the compounds and their physiologically acceptable salts and solvates may be formulated for administration by, for example, solid dosing, eyedrop, in a topical oil-based formulation, injection, inhalation (either through the mouth or the nose), implants, or oral, buccal, parenteral or rectal administration. Techniques and formulations may generally be found in "Remington's Pharmaceutical Sciences", (Meade Publishing Co., Easton, Pa.). Therapeutic compositions must typically be sterile and stable under the conditions of manufacture and storage.

Compositions of the present invention may comprise a safe and effective amount of the subject compounds, and a pharmaceutically-acceptable carrier. As used herein, "safe and effective amount" means an amount of a compound sufficient to significantly induce a positive modification in the condition to be treated, but low enough to avoid serious side effects (at a reasonable benefit/risk ratio), within the scope of sound medical judgment. A safe and effective amount of a compound will vary with the particular condition being treated, the age and physical condition of the patient being treated, the severity of the condition, the duration of treatment, the nature of concurrent therapy, the particular pharmaceutically-acceptable carrier utilized, and like factors within the knowledge and expertise of the attending physician.

The route by which the compounds of the present invention (component A) will be administered and the form of the composition will dictate the type of carrier (component B) to be used. The composition may be in a variety of forms, suitable, for example, for systemic administration (e.g., oral, rectal, nasal, sublingual, buccal, implants, or parenteral) or topical administration (e.g., local application on the skin, ocular, liposome delivery systems, or iontophoresis).

Carriers for systemic administration typically comprise at least one of a) diluents, b) lubricants, c) binders, d) disintegrants, e) colorants, f) flavors, g) sweeteners, h) antioxidants, j) preservatives, k) glidants, m) solvents, n) suspending agents, o) wetting agents, p) surfactants, combinations thereof, and others. All carriers are optional in the systemic compositions.

Ingredient a) is a diluent. Suitable diluents for solid dosage forms include sugars such as glucose, lactose, dextrose, and sucrose; diols such as propylene glycol; calcium carbonate; sodium carbonate; sugar alcohols, such as glycerin; mannitol; and sorbitol. The amount of ingredient a) in the systemic or topical composition is typically about 50 to about 90%.

Ingredient b) is a lubricant. Suitable lubricants for solid dosage forms are exemplified by solid lubricants including silica, talc, stearic acid and its magnesium salts and calcium salts, and calcium sulfate; and liquid lubricants such as polyethylene glycol and vegetable oils (e.g., peanut oil, cottonseed oil, sesame oil, olive oil, corn oil and oil of theobroma). The amount of ingredient b) in the systemic or topical composition is typically about 5 to about 10%.

Ingredient c) is a binder. Suitable binders for solid dosage forms include polyvinyl pyrrolidone; magnesium aluminum silicate; starches such as corn starch and potato starch; gelatin; tragacanth; and cellulose and its derivatives, such as sodium carboxymethylcellulose, ethyl cellulose, methylcellulose, microcrystalline cellulose, and sodium carboxymethylcellulose. The amount of ingredient c) in the systemic composition is typically about 5 to about 50%, and in ocular solid dosing forms up to about 99%.

Ingredient d) is a disintegrant. Suitable disintegrants for solid dosage forms include agar, alginic acid and the sodium salt thereof, effervescent mixtures, croscarmelose, crospovidone, sodium carboxymethyl starch, sodium starch glycolate, clays, and ion exchange resins. The amount of ingredient d) in the systemic or topical composition is typically about 0.1 to about 10%.

Ingredient e) for solid dosage forms is a colorant such as an FD&C dye. When used, the amount of ingredient e) in the systemic or topical composition is typically about 0.005 to about 0.1%.

Ingredient f) for solid dosage forms is a flavor such as menthol, peppermint, and fruit flavors. The amount of ingredient f), when used, in the systemic or topical composition is typically about 0.1 to about 1.0%.

Ingredient g) for solid dosage forms is a sweetener such as aspartame and saccharin. The amount of ingredient g) in the systemic or topical composition is typically about 0.001 to about 1%.

Ingredient h) is an antioxidant such as butylated hydroxyanisole ("BHA"), butylated hydroxytoluene ("BHT"), and vitamin E. The amount of ingredient h) in the systemic or topical composition is typically about 0.1 to about 5%.

Ingredient j) is a preservative such as benzalkonium chloride, methyl paraben and sodium benzoate. The amount of ingredient j) in the systemic or topical composition is typically about 0.01 to about 5%.

Ingredient k) for solid dosage forms is a glidant such as silicon dioxide. The amount of ingredient k) in the systemic or topical composition is typically about 1 to about 5%.

Ingredient m) is a solvent, such as water, isotonic saline, ethyl oleate, glycerine, hydroxylated castor oils, alcohols such as ethanol, and phosphate buffer solutions. The amount of ingredient m) in the systemic or topical composition is typically from about 0 to about 100%.

Ingredient n) is a suspending agent. Suitable suspending agents include AVICEL® RC-591 (from FMC Corporation of Philadelphia, Pa.) and sodium alginate. The amount of ingredient n) in the systemic or topical composition is typically about 1 to about 8%.

Ingredient o) is a wetting agent such as sodium lauryl sulfate, polyoxyethylene sorbitan fatty acid esters, polyoxyethylene alkyl ethers, sorbitan fatty acid esters, polyethylene glycols, polyoxyethylene castor oil derivatives, docusate sodium, quaternary ammonium compounds, sugar esters of fatty acids and glycerides of fatty acids.

Ingredient p) is a surfactant such as lecithin, Polysorbate 80, and sodium lauryl sulfate, and the TWEENS® from Atlas Powder Company of Wilmington, Del. Suitable surfactants include those disclosed in the C.T.F.A. Cosmetic Ingredient Handbook, 1992, pp. 587-592; Remington's Pharmaceutical Sciences, 15th Ed. 1975, pp. 335-337; and McCutcheon's Volume 1, Emulsifiers & Detergents, 1994, North American Edition, pp. 236-239. The amount of ingredient p) in the systemic or topical composition is typically about 0.1% to about 5%.

Although the amounts of components A and B in the systemic compositions will vary depending on the type of systemic composition prepared, the specific derivative selected for component A and the ingredients of component B, in general, system compositions comprise about 0.001% to about 50% of component A and about 50 to about 99.99% of component B.

Compositions for parenteral administration typically comprise about 0.001 to about 10% of component A and about 90 to about 99.99% of component B comprising a) a diluent and m) a solvent. In one embodiment, component a) comprises propylene glycol and m) comprises ethanol or ethyl oleate.

Compositions for oral administration can have various dosage forms. For example, solid forms include tablets, capsules, granules, and bulk powders. These oral dosage forms comprise a safe and effective amount, usually at least about 5%, and more particularly from about 25% to about 50% of component A. The oral dosage compositions further comprise about 50 to about 95% of component B, and more particularly, from about 50 to about 75%.

Tablets can be compressed, tablet triturates, enteric-coated, sugar-coated, film-coated, or multiple-compressed. Tablets typically comprise component A, and component B a carrier comprising ingredients selected from the group consisting of a) diluents, b) lubricants, c) binders, d) disintegrants, e) colorants, f) flavors, g) sweeteners, k) glidants, and combinations thereof. Specific diluents include calcium carbonate, sodium carbonate, mannitol, lactose and cellulose. Specific binders include starch, gelatin, and sucrose. Specific disintegrants include alginic acid and croscarmelose. Specific lubricants include magnesium stearate, stearic acid, and talc. Specific colorants are the FD&C dyes, which can be added for appearance. Chewable tablets preferably contain g) sweeteners such as aspartame and saccharin, or f) flavors such as menthol, peppermint, fruit flavors, or a combination thereof.

Capsules (including implants, time release and sustained release formulations) typically comprise component A, and a carrier comprising one or more a) diluents disclosed above in a capsule comprising gelatin. Granules typically comprise component A, and preferably further comprise k) glidants such as silicon dioxide to improve flow characteristics. Implants can be of the biodegradable or the non-biodegradable type. Implants may be prepared using any known biocompatible formulation.

The solid compositions may also be coated by conventional methods, typically with pH or time-dependent coatings, such that component A is released in the gastrointestinal tract in the vicinity of the desired application, or at various points and times to extend the desired action. The coatings typically comprise one or more components selected from the group consisting of cellulose acetate phthalate, polyvinyl acetate phthalate, hydroxypropyl methyl cellulose phthalate, ethyl cellulose, EUDRAGIT® coatings (available from Rohm & Haas G.M.B.H. of Darmstadt, Germany), waxes and shellac.

Compositions for oral administration can also have liquid forms. For example, suitable liquid forms include aqueous solutions, emulsions, suspensions, solutions reconstituted from non-effervescent granules, suspensions reconstituted from non-effervescent granules, effervescent preparations reconstituted from effervescent granules, elixirs, tinctures, syrups, and the like. Liquid orally administered compositions typically comprise component A and component B, namely, a carrier comprising ingredients selected from the group consisting of a) diluents, e) colorants, f) flavors, g) sweeteners, j) preservatives, m) solvents, n) suspending agents, and p) surfactants. Peroral liquid compositions preferably comprise one or more ingredients selected from the group consisting of e) colorants, f) flavors, and g) sweeteners.

The selection of ingredients in the carrier for oral compositions depends on secondary considerations like taste, cost, and shelf stability, which are not critical for the purposes of this invention. One skilled in the art would know how to select appropriate ingredients without undue experimentation.

Other compositions useful for attaining systemic delivery of the subject compounds include sublingual, buccal and nasal dosage forms. Such compositions typically comprise one or more of soluble filler substances such as a) diluents including sucrose, sorbitol and mannitol; and c) binders such as acacia, microcrystalline cellulose, carboxymethyl cellulose, and hydroxypropyl methylcellulose. Such compositions may further comprise b) lubricants, e) colorants, f) flavors, g) sweeteners, h) antioxidants, and k) glidants.

In one embodiment of the invention, the compounds of the present invention are topically administered. Topical compositions that can be applied locally to the eye may be in any form known in the art, non-limiting examples of which include solids, gelable drops, sprays, ointments, or a sustained or non-sustained release unit placed in the conjunctival cul-du-sac of the eye or another appropriate location.

Topical compositions that can be applied locally to the skin may be in any form including solids, solutions, oils, creams, ointments, gels, lotions, shampoos, leave-on and rinse-out hair conditioners, milks, cleansers, moisturizers, sprays, skin patches, and the like. Topical compositions comprise: component A, the compounds described above, and component B, a carrier. The carrier of the topical composition preferably aids penetration of the compounds into the eye and through the skin. Component B may further comprise one or more optional components.

The exact amounts of each component in the topical composition depend on various factors. The amount of component A added to the topical composition is dependent on the $IC_{50}$ of component A, typically expressed in nanomolar (nM) units. For example, if the $IC_{50}$ of the medicament is 1 nM, the amount of component A will be from about 0.001 to about 0.3%. If the $IC_{50}$ of the medicament is 10 nM, the amount of component A will be from about 0.01 to about 1%. If the $IC_{50}$ of the medicament is 100 nM, the amount of component A will be from about 0.1 to about 10%. If the $IC_{50}$ of the medicament is 1000 nM, the amount of component A will be from about 1 to about 100%, preferably about 5% to about 50%. If the amount of component A is outside the ranges specified above (i.e., lower), efficacy of the treatment may be reduced. One skilled in the art understands how to calculate and understand an $IC_{50}$. The remainder of the composition, up to 100%, is component B.

The amount of the carrier employed in conjunction with component A is sufficient to provide a practical quantity of composition for administration per unit dose of the medicament. Techniques and compositions for making dosage forms useful in the methods of this invention are described in the following references: *Modern Pharmaceutics*, Chapters 9 and 10, Banker & Rhodes, eds. (1979); Lieberman et al., *Pharmaceutical Dosage Forms: Tablets* (1981); and Ansel, *Introduction to Pharmaceutical Dosage Forms*, $2^{nd}$ Ed., (1976).

Component B may comprise a single ingredient or a combination of two or more ingredients. In the topical compositions, component B comprises a topical carrier. Suitable topical carriers comprise one or more ingredients selected from the group consisting of phosphate buffered saline, isotonic water, deionized water, monofunctional alcohols, symmetrical alcohols, aloe vera gel, allantoin, glycerin, vitamin A and E oils, mineral oil, propylene glycol, PPG-2 myristyl propionate, dimethyl isosorbide, castor oil, combinations thereof, and the like. More particularly, carriers for skin applications include propylene glycol, dimethyl isosorbide, and water, and even more particularly, phosphate buffered saline, isotonic water, deionized water, monofunctional alcohols and symmetrical alcohols.

The carrier of the topical composition may further comprise one or more ingredients selected from the group consisting of q) emollients, r) propellants, s) solvents, t) humectants, u) thickeners, v) powders, w) fragrances, x) pigments, and y) preservatives.

Ingredient q) is an emollient. The amount of ingredient q) in a skin-based topical composition is typically about 5 to about 95%. Suitable emollients include stearyl alcohol, glyceryl monoricinoleate, glyceryl monostearate, propane-1,2-diol, butane-1,3-diol, mink oil, cetyl alcohol, isopropyl isostearate, stearic acid, isobutyl palmitate, isocetyl stearate, oleyl alcohol, isopropyl laurate, hexyl laurate, decyl oleate, octadecan-2-ol, isocetyl alcohol, cetyl palmitate, di-n-butyl sebacate, isopropyl myristate, isopropyl palmitate, isopropyl stearate, butyl stearate, polyethylene glycol, triethylene glycol, lanolin, sesame oil, coconut oil, arachis oil, castor oil, acetylated lanolin alcohols, petroleum, mineral oil, butyl myristate, isostearic acid, palmitic acid, isopropyl linoleate, lauryl lactate, myristyl lactate, decyl oleate, myristyl myristate, and combinations thereof. Specific emollients for skin include stearyl alcohol and polydimethylsiloxane.

Ingredient r) is a propellant. The amount of ingredient r) in the topical composition is typically about 0 to about 95%. Suitable propellants include propane, butane, isobutane, dimethyl ether, carbon dioxide, nitrous oxide, and combinations thereof.

Ingredient s) is a solvent. The amount of ingredient s) in the topical composition is typically about 0 to about 95%. Suitable solvents include water, ethyl alcohol, methylene chloride, isopropanol, castor oil, ethylene glycol monoethyl ether, diethylene glycol monobutyl ether, diethylene glycol monoethyl ether, dimethylsulfoxide, dimethyl formamide, tetrahydrofuran, and combinations thereof. Specific solvents include ethyl alcohol and homotopic alcohols.

Ingredient t) is a humectant. The amount of ingredient t) in the topical composition is typically about 0 to about 95%. Suitable humectants include glycerin, sorbitol, sodium 2-pyrrolidone-5-carboxylate, soluble collagen, dibutyl phthalate, gelatin, and combinations thereof. Specific humectants include glycerin.

Ingredient u) is a thickener. The amount of ingredient u) in the topical composition is typically about 0 to about 95%.

Ingredient v) is a powder. The amount of ingredient v) in the topical composition is typically about 0 to about 95%. Suitable powders include beta-cyclodextrins, hydroxypropyl cyclodextrins, chalk, talc, fullers earth, kaolin, starch, gums, colloidal silicon dioxide, sodium polyacrylate, tetra alkyl ammonium smectites, trialkyl aryl ammonium smectites, chemically-modified magnesium aluminum silicate, organically-modified Montmorillonite clay, hydrated aluminum silicate, fumed silica, carboxyvinyl polymer, sodium carboxymethyl cellulose, ethylene glycol monostearate, and combinations thereof. For ocular applications, specific powders include beta-cyclodextrin, hydroxypropyl cyclodextrin, and sodium polyacrylate. For gel dosing ocular formulations, sodium polyacrylate may be used.

Ingredient w) is a fragrance. The amount of ingredient w) in the topical composition is typically about 0 to about 0.5%, particularly, about 0.001 to about 0.1% %. For ocular applications a fragrance is not typically used.

Ingredient x) is a pigment. Suitable pigments for skin applications include inorganic pigments, organic lake pigments, pearlescent pigments, and mixtures thereof. Inorganic pigments useful in this invention include those selected from the group consisting of rutile or anatase titanium dioxide, coded in the Color Index under the reference CI 77,891; black, yellow, red and brown iron oxides, coded under references CI 77,499, 77,492 and, 77,491; manganese violet (CI 77,742); ultramarine blue (CI 77,007); chromium oxide (CI 77,288); chromium hydrate (CI 77,289); and ferric blue (CI 77,510) and mixtures thereof.

Suitable organic pigments and lakes include, but are not limited to D&C Red No. 19 (CI 45,170), D&C Red No. 9 (CI 15,585), D&C Red No. 21 (CI 45,380), D&C Orange No. 4 (CI 15,510), D&C Orange No. 5 (CI 45,370), D&C Red No. 27 (CI 45,410), D&C Red No. 13 (CI 15,630), D&C Red No. 7 (CI 15,850), D&C Red No. 6 (CI 15,850), D&C Yellow No. 5 (CI 19,140), D&C Red No. 36 (CI 12,085), D&C Orange No. 10 (CI 45,425), D&C Yellow No. 6 (CI 15,985), D&C Red No. 30 (CI 73,360), D&C Red No. 3 (CI 45,430), the dye or lakes based on Cochineal Carmine (CI 75,570) and mixtures thereof.

The pearlescent pigments useful in this invention include those selected from the group consisting of the white pearlescent pigments such as mica coated with titanium oxide, bismuth oxychloride, colored pearlescent pigments such as titanium mica with iron oxides, titanium mica with ferric blue, chromium oxide and the like, titanium mica with an organic pigment of the above-mentioned type as well as those based on bismuth oxychloride and mixtures thereof. The amount of pigment in the topical composition is typically about 0 to about 10%. For ocular applications a pigment is generally not used.

In a particularly preferred embodiment of the invention, topical pharmaceutical compositions for ocular administration are prepared typically comprising component A and B (a carrier), such as purified water, and one or more ingredients selected from the group consisting of y) sugars or sugar alcohols such as dextrans, particularly mannitol and dextran 70, z) cellulose or a derivative thereof, aa) a salt, bb) disodium EDTA (Edetate disodium), and cc) a pH adjusting additive.

Examples of z) cellulose derivatives suitable for use in the topical pharmaceutical composition for ocular administration include sodium carboxymethylcellulose, ethylcellulose, methylcellulose, and hydroxypropyl-methylcellulose, particularly, hydroxypropyl-methylcellulose.

Examples of aa) salts suitable for use in the topical pharmaceutical composition for ocular administration include mono-, di- and trisodium phosphate, sodium chloride, potassium chloride, and combinations thereof.

Examples of cc) pH adjusting additives include HCl or NaOH in amounts sufficient to adjust the pH of the topical pharmaceutical composition for ocular administration to 5.0-7.5.

The dosage range of the compound for systemic administration is from about 0.01 to about 1000 µg/kg body weight, preferably from about 0.1 to about 100 µg/kg per body weight, most preferably from about 1 to about 50 µg/kg body weight per day. The transdermal dosages will be designed to attain similar serum or plasma levels, based upon techniques known to those skilled in the art of pharmacokinetics and transdermal formulations. Plasma levels for systemic administration are expected to be in the range of 0.01 to 100 nanograms/mL, (ng/mL) more preferably from 0.05 to 50 ng/mL and most preferably from 0.1 to 10 ng/mL. While these dosages are based upon a daily administration rate, weekly or monthly accumulated dosages may also be used to calculate the clinical requirements.

Dosages may be varied based on the patient being treated, the condition being treated, the severity of the condition being treated, the route of administration, etc. to achieve the desired effect.

The compounds of the present invention are useful in decreasing intraocular pressure. Thus, these compounds are useful in the treatment of glaucoma. The preferred route of administration for treating glaucoma is topically.

Component A may be included in kits comprising component A, a systemic or topical composition described above, or both; and information, instructions, or both that use of the kit will provide treatment for cosmetic and medical conditions in mammals (particularly humans). The information and instructions may be in the form of words, pictures, or both, and the like. In addition, or in the alternative, the kit may comprise the medicament, a composition, or both; and information, instructions, or both, regarding methods of application of medicament, or of composition, preferably with the benefit of treating or preventing cosmetic and medical conditions in mammals (e.g., humans).

The invention will be further explained by the following illustrative examples that are to be considered to be non-limiting.

EXAMPLES

Procedures for preparation of the 6- or 7-aminoisoquinolines are described in the following examples. All temperatures are in degrees Centigrade. Reagents and starting materials were purchased from commercial sources or prepared following published literature procedures.

Unless otherwise noted, HPLC purification, when appropriate, was performed by redissolving the compound in a small volume of DMSO and filtering through a 0.45 micron (nylon disc) syringe filter. The solution was then purified using, for example, a 50 mm Varian Dynamax HPLC 21.4 mm Micro sorb Guard-8 $C_8$ column (Sigma-Aldrich Corporation, St. Louis, Mo.). A typical initial eluting mixture of 40-80% MeOH:$H_2O$ was selected as appropriate for the target compound. This initial gradient was maintained for 0.5 minutes then increased to 100% MeOH: 0% $H_2O$ over 5 minutes. 100% MeOH was maintained for 2 more minutes before re-equilibration back to the initial starting gradient. A typical total run time was 8 minutes. The resulting fractions were analyzed, combined as appropriate, and then evaporated to provide purified material.

Proton magnetic resonance ($^1$H NMR) spectra were recorded on either a Varian INOVA 600 MHz ($^1$H) NMR spectrometer, Varian INOVA 500 MHz ($^1$H) NMR spectrometer, Varian Mercury 300 MHz (1H) NMR spectrometer, or a Varian Mercury 200 MHz ($^1$H) NMR spectrometer. All spectra were determined in the solvents indicated. Although chemical shifts are reported in ppm downfield of tetramethylsilane, they are referenced to the residual proton peak of the respective solvent peak for $^1$H NMR. Interproton coupling constants are reported in Hertz (Hz).

Analytical LCMS spectra were obtained using a Waters ZQ MS ESI instrument with an Alliance 2695 HPLC and a 2487 dual wavelength UV detector. Spectra were analyzed at 254 and 230 nm. Samples were passed through a Waters Symmetry C18 4.6×75 mm 3.5µ column (Sigma-Aldrich Corporation, St. Louis, Mo.) with or without a guard column (3.9×20 mm 5µ). Gradients were run with mobile phase A: 0.1% formic acid in $H_2O$ and mobile phase B: ACN (acetonitrile) with a flow rate of 0.8 mL/min. Two gradients will illustrate:

| Gradient A | | | Gradient B | | |
| --- | --- | --- | --- | --- | --- |
| Time | A % | B % | Time | A % | B % |
| 0.00 | 80.0 | 20.0 | 0.00 | 80.0 | 20.0 |
| 1.00 | 80.0 | 20.0 | 1.00 | 80.0 | 20.0 |
| 6.00 | 25.0 | 75.0 | 6.00 | 25.0 | 75.0 |
| 7.00 | 5.0 | 95.0 | 7.00 | 5.0 | 95.0 |
| 8.00 | 5.0 | 95.0 | 8.00 | 5.0 | 95.0 |
| 9.00 | 80.0 | 20.0 | 9.00 | 80.0 | 20.0 |
| 12.00 | 80.0 | 20.0 | 12.00 | 80.0 | 20.0 |

The settings for the MS probe were a cone voltage at 38 mV and a desolvation temperature at 250° C. Any variations in these methods are noted below.

The following preparations illustrate procedures for the preparation of intermediates and methods for the preparation of 6- and 7-aminoisoquinolines.

Example 1

Preparation of (R)-tert-butyl-2-(isoquinolin-6-ylamino)-2-oxo-1 phenyl-ethylcarbamate (E1)

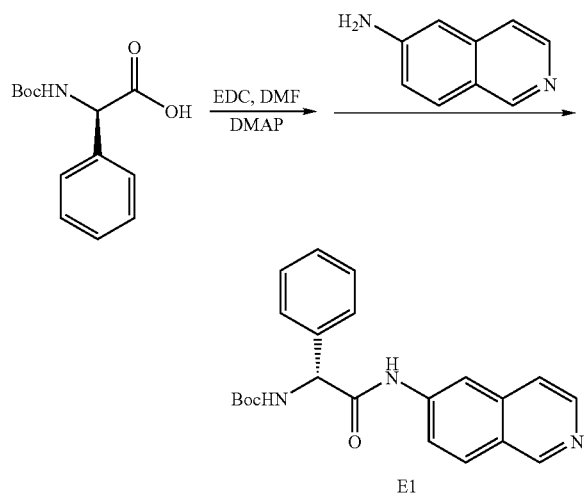

To (R)-2-Boc-2-phenylacetic acid in DMF was added EDC, dimethyl aminopyridine ("DMAP") and 6-aminoisoquinoline. This mixture was stirred for 4 hours and the reaction was washed with NaHCO$_3$ (sat), extracted with EtOAc, dried (Na$_2$SO$_4$), filtered and evaporated. Column chromatography (SiO$_2$, Hexanes/EtOAc) gave pure (R)-tert-butyl-2-(isoquinolin-6-ylamino)-2-oxo-1 phenyl-ethylcarbamate (E1).

Example 2

Preparation of (R)-2-amino-N-(isoquinolin-6-yl)-2-phenylacetamide dihydrochloride (E2)

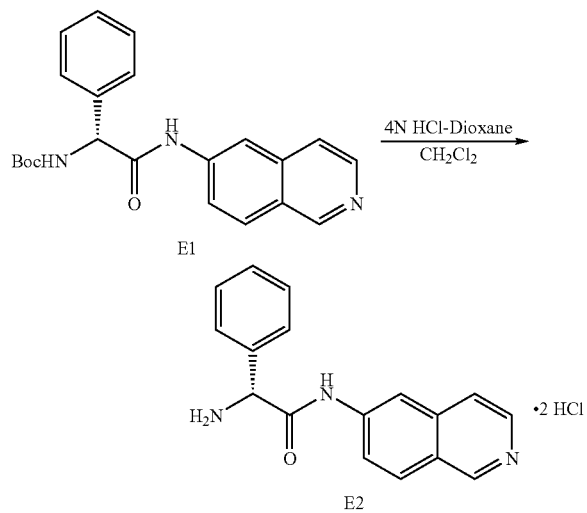

To (R)-tert-butyl-2-(isoquinolin-6-ylamino)-2-oxo-1 phenyl-ethylcarbamate (E1) in CH$_2$Cl$_2$ was added HCl (4M in dioxane) and the solution was stirred overnight at room temperature. The reaction was concentrated to give (R)-2-amino-N-(isoquinolin-6-yl)-2-phenylacetamide dihydrochloride (E2).

Example 3

Preparation of (R)-2-(dimethylamino)-N-(isoquinolin-6-yl)-2-phenylacetamide dihydrochloride (E3)

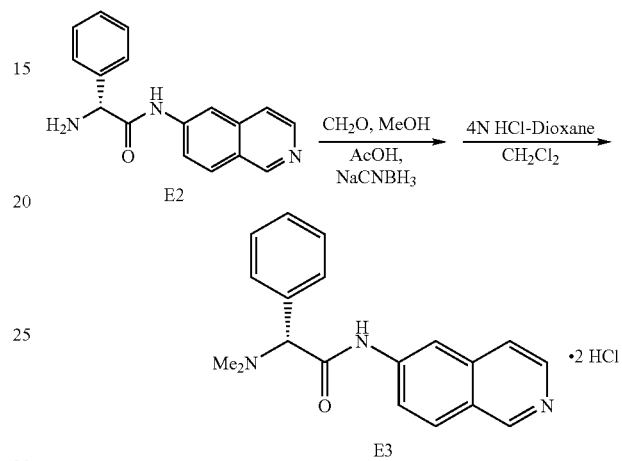

To (R)-2-amino-N-(isoquinolin-6-yl)-2-phenylacetamide dihydrochloride (E2) in MeOH was added CH$_2$O (37%), AcOH and NaCNBH$_3$. After stirring for 1.5 hours the solution was poured into NaHCO$_3$(sat) and extracted with EtOAc, dried (Na$_2$SO$_4$), filtered and concentrated. Column chromatography Hexanes/EtOAc gave pure (R)-2-(dimethylamino)-N-(isoquinolin-6-yl)-2-phenylacetamide. To (R)-2-(dimethylamino)-N-(isoquinolin-6-yl)-2-phenylacetamide was added CH$_2$Cl$_2$ and HCl (4N in dioxane) and the solvents were evaporated to give pure (R)-2-(dimethylamino)-N-(isoquinolin-6-yl)-2-phenylacetamide dihydrochloride (E3).

Example 4

Preparation of (R)-methyl 2-(tert-butoxycarbonylamino)-2-phenylacetate (E4)

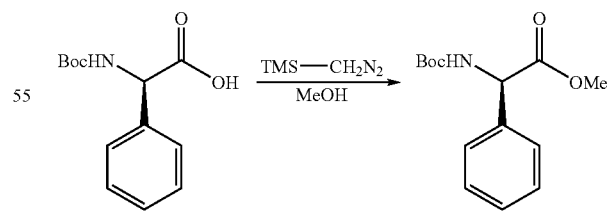

To (R)-2-Boc-2-phenylacetic acid in MeOH was added TMS-CH$_2$N$_2$ until the solution maintained a persistent yellow color. Then the mixture was stirred at room temperature for 1 hour and excess TMS-CH$_2$N$_2$ was quenched with AcOH. The solvents were evaporated and column chromatography Hexanes/EtOAc gave pure (R)-methyl 2-(tert-butoxycarbonylamino)-2-phenylacetate (E4).

Example 5

Preparation of (R)-methyl 2-(tert-butoxycarbonyl(methyl)amino)-2-phenylacetate (E5)

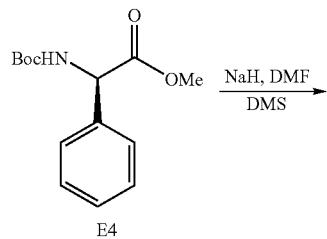

E4

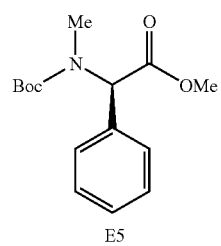

E5

To (R)-methyl 2-(tert-butoxycarbonylamino)-2-phenylacetate (E4) in DMF at −40° C. was added NaH and the solution was warmed to 0° C. for 20 minutes. DMS was added and solution was stirred at room temperature for 3 hours. The mixture was poured into NH₄Cl(sat)/HCl (1N) 3:1 and extracted with EtOAc. The organics were dried (Na₂SO₄), filtered and evaporated to give crude E5. Column chromatography Hexanes/EtOAc gave pure (R)-methyl 2-(tert-butoxycarbonyl(methyl)amino)-2-phenylacetate (E5).

Example 6

Preparation of (R)-2-(tert-butoxycarbonyl(methyl)amino)-2-phenylacetate (E6)

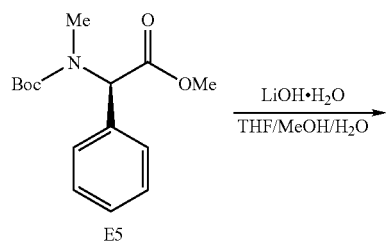

E5

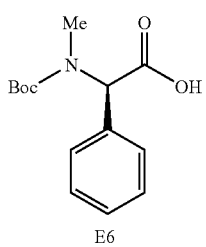

E6

To (R)-methyl 2-(tert-butoxycarbonyl(methyl)amino)-2-phenylacetate (E5) in THF/H₂O/MeOH at 0° C. was added LiOH.H₂O and solution was allowed to warm and stir at room temperature for 4 hours. The mixture was acidified with HCl to pH 3-4 and extracted with EtOAc, dried (Na₂SO₄), filtered and evaporated to give (R)-2-(tert-butoxycarbonyl(methyl)amino)-2-phenylacetate (E6).

Example 7

Preparation of (R)-tert-butyl 2-(isoquinolin-6-ylamino)-2-oxo-1-phenylethyl(methyl)carbamate (E7)

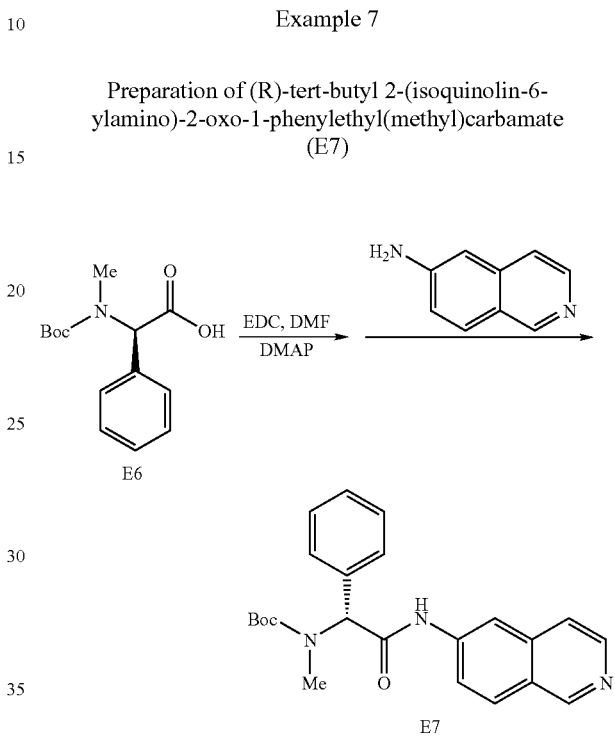

E7

To (R)-2-(tert-butoxycarbonyl(methyl)amino)-2-phenylacetate (E6) in DMF was added EDC, DMAP and 6-aminoisoquinoline. This mixture was stirred for 4 hours and the reaction was washed with NaHCO₃ (sat), extracted with EtOAc, dried (Na₂SO₄), filtered and evaporated. Column chromatography (SiO₂, Hexanes/EtOAc) gave pure (R)-tert-butyl 2-(isoquinolin-6-ylamino)-2-oxo-1-phenylethyl(methyl)carbamate (E7).

Example 8

Preparation of (R)-N-(isoquinolin-6-ylamino)-2-(methylamino)-2-phenyl acetamide dihydrochloride (E8)

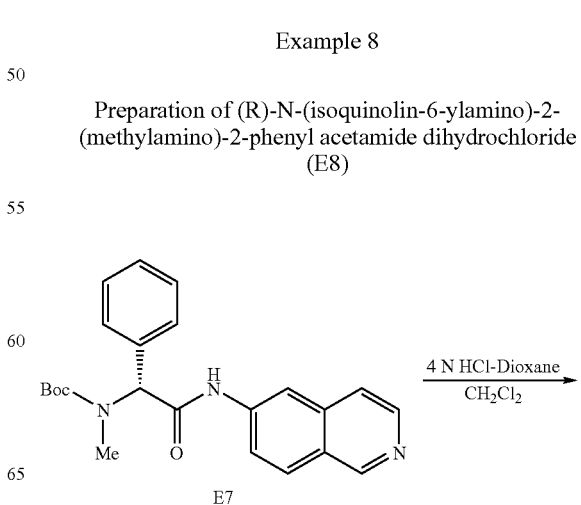

E7

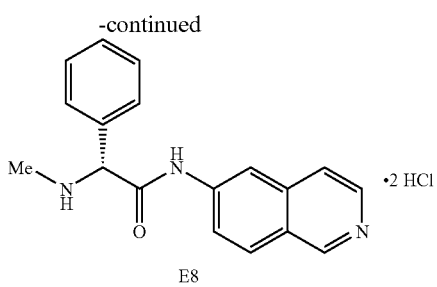

E8

To (R)-tert-butyl 2-(isoquinolin-6-ylamino)-2-oxo-1-phenylethyl(methyl) carbamate (E7) in CH₂Cl₂ was added HCl (4M in dioxane) and the solution was stirred overnight at room temperature. The reaction was concentrated to give (R)-N-(isoquinolin-6-ylamino)-2-(methylamino)-2-phenyl acetamide dihydrochloride (E8).

Similarly, using largely the procedures set forth in Examples 1-8 and substituting the appropriate starting materials, the compounds listed below can be made.

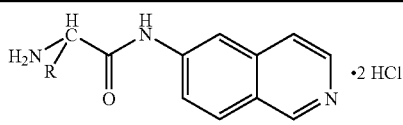

| Example No. | R |
|---|---|
| 9, 10, 11, 12, 13, 14, 15, 16 | cyclohexyl, cyclopentyl, cyclopropyl, furyl, o-aminophenyl, p-aminophenyl, thienyl, benzofuryl, benzothienyl |

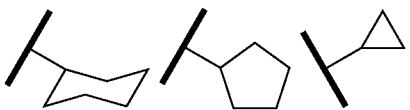

| Example No. | B | R |
|---|---|---|
| 17 | CH₃ | o-F-C₆H₄— |
| 18 | CH₂CH₃ | p-Me-C₆H₄— |
| 19 | CH₂CH₂CH₃ | m-F-C₆H₄— |
| 20 | CH₂CH₂CH₂CH₃ | p-Br-C₆H₄— |
| 21 | CH(Me)—CH₂CH₃ | o-Me-C₆H₄— |
| 22 | CH(Et)CH₂CH₃ | p-Et-C₆H₄— |
| 23 | CH₂CH₂CH₃ | p-MeO-C₆H₄— |
| 24 | CH₃ | o-iPr-C₆H₄— |
| 25 | CH₂CH₂CH₃ | cyclohexyl |
| 26 | CH₃ | cyclopentyl |
| 27 | —CH₂-Ph | cyclopropyl |

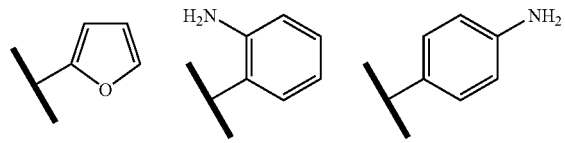

| Example No. | B | R |
|---|---|---|
| 28 | CH₃ | C₆H₅— |
| 29 | CH₃ | p-Me-C₆H₄— |
| 30 | CH₃ | m-F-C₆H₄— |
| 31 | CH₃ | p-Br-C₆H₄— |
| 32 | CH₃ | o-Me-C₆H₄— |
| 33 | CH₃ | p-Et-C₆H₄— |
| 34 | CH₃ | p-MeO-C₆H₄— |
| 35 | CH₃ | o-iPr-C₆H₄— |
| 36 | CH₂CH₂CH₃ | cyclohexyl |
| 37 | CH₃ | cyclopentyl |
| 38 | —CH₂-Ph | cyclopropyl |

Example 39

Preparation of N-(isoquinolin-6-yl)-2-morpholino-2-phenyl-acetamide

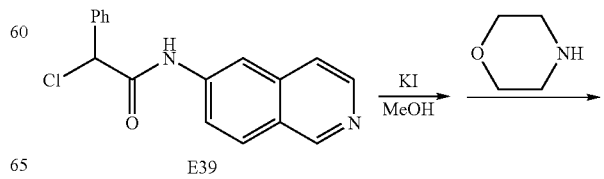

E39

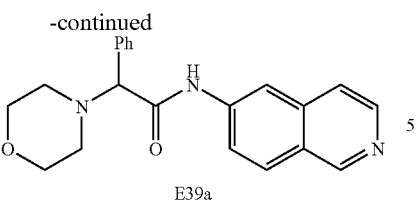

E39a

To 2-chloro-2-phenyl-N-(isoquinolin-6-yl)acetamide (E39) in MeOH is added KI and the solution is heated to 60° C. for 40 minutes. The mixture is cooled to 45° C. and morpholine is added and stirred at 45° C. After 2-4 hours, the solvents are evaporated and the residue is taken up in EtOAc and extracted with NaHCO$_3$(sat). The organics are dried (Na$_2$SO$_4$), filtered and evaporated. Flash chromatography (2% NH$_3$(2M)/MeOH/3% MeOH/CH$_2$Cl$_2$) gives N-(isoquinolin-6-yl)-2-morpholino-2-phenyl-acetamide (E39a).

Using largely the procedure set forth in Example 39 and substituting the appropriate starting materials, the compounds 40-49 can be made.

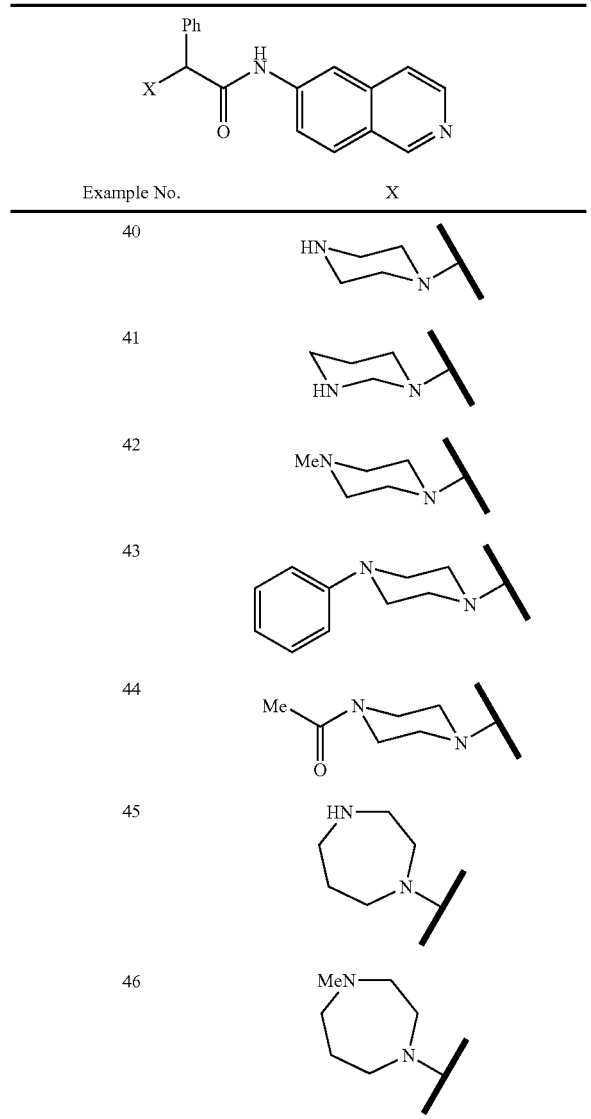

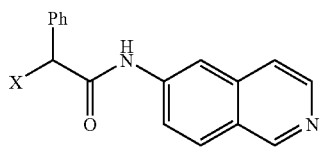

| Example No. | X |
|---|---|
| 47 | 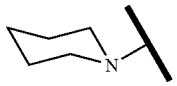 |
| 48 | 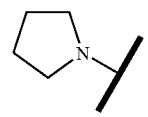 |
| 49 | 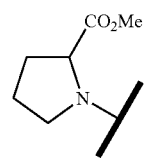 |

Reference Example One

The cell-based porcine trabecular meshwork (PTM) assay.

The anterior section of porcine eyes was harvested within 4 hours post-mortem. The iris and ciliary body were removed and trabecular meshwork cells were harvested by blunt dissection. Finely minced trabecular meshwork tissue was plated into collagen-coated 6-well plates in Medium-199 containing 20% fetal bovine serum (FBS). After two passages at confluence, cells were transferred to low-glucose DMEM containing 10% FBS. Cells were used between passage 3 and passage 8.

Cells were plated into fibronectin-coated, glass multiwell plates the day before compound testing under standard culture conditions. Compounds were added to cells in the presence of 1% FBS-containing DMEM and 1% DMSO. When compounds were incubated with the cells for the duration determined to be optimal, the media and compounds were removed and cells fixed for 20 minutes in 3% methanol-free paraformaldehyde. Cells were rinsed twice with phosphate buffered saline (PBS) and the cells were permeabilized with 0.5% Triton X-100 for two minutes. Following an additional two washes with PBS, F-actin was stained with Alexa-fluor 488-labelled phalloidin and nuclei were stained with DAPI.

Data were reduced to the mean straight actin-fiber length and normalized to DMSO-treated control cells (100%) and 50 μM Y-27632 (0%). Y-27632 is a rho-kinase inhibitor known to result in the depolymerization of F-actin in these cells.

Example 50

Preparation of N-(isoquinolin-6-yl)cyclohexylamino phenylmethanesulfonamide. (E50)

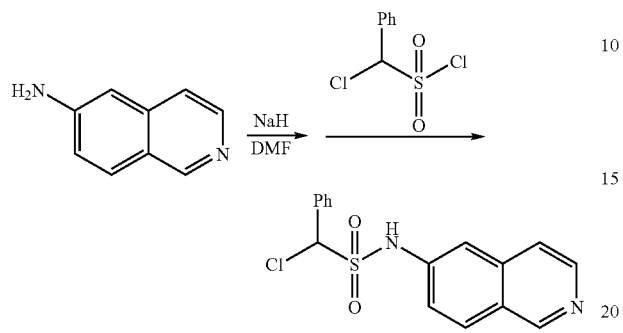

To 6-aminoisoquinoline in DMF at 0° C. is added NaH. After 30 min, chloro(phenyl)methylsulfonyl chloride is added to the reaction. After 2-4 hours at rt or when TLC indicates completion, the reaction is quenched by the addition of water and extracted with EtOAc. The combined organics are washed with brine and dried (Na$_2$SO$_4$), filtered and evaporated. Column chromatography (SiO$_2$, 5% MeOH/CH$_2$Cl$_2$) gives 1-chloro-N-(isoquinolin-6-yl) phenylmethanesulfonamide.

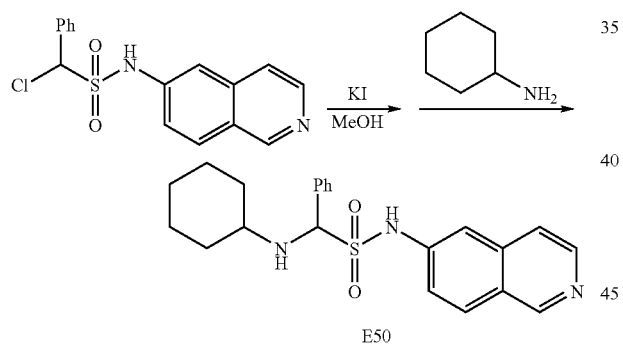

E50

To 1-chloro-N-(isoquinolin-6-yl) phenylmethanesulfonamide in MeOH is added KI and the solution is heated to 60° C. for 40 minutes. The mixture is cooled to 45° C. and cyclohexylamine is added and stirred at 45° C. After 2-4 hours or when TLC indicated completion of the reaction, the solvents are evaporated and the residue is taken up in EtOAc and extracted with NaHCO$_3$ (sat). The organics are dried (Na$_2$SO$_4$), filtered and evaporated. Flash chromatography (SiO$_2$, 2% NH$_3$(2M) in MeOH/3% MeOH/CH$_2$Cl$_2$) gives N-(isoquinolin-6-yl)cyclohexylamino phenylmethanesulfonamide (E50).

Examples 51-55

Using the general procedure shown for Example 50, the following compounds can be synthesized from the corresponding 6-aminoisoquinoline.

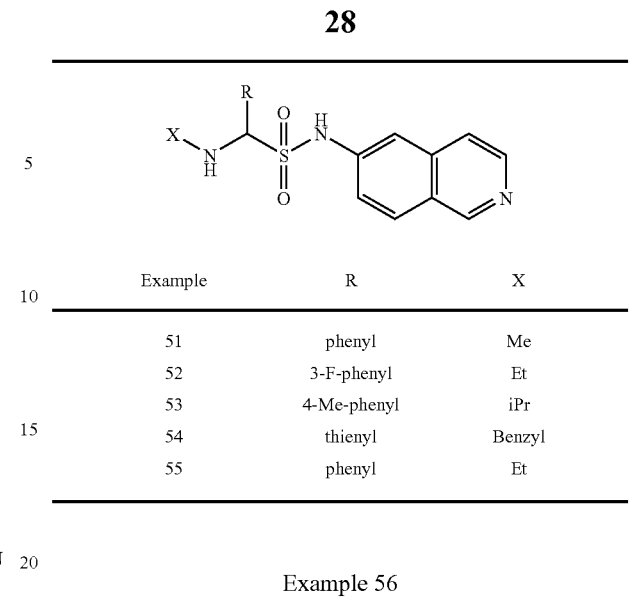

| Example | R | X |
|---------|-----------|--------|
| 51 | phenyl | Me |
| 52 | 3-F-phenyl | Et |
| 53 | 4-Me-phenyl | iPr |
| 54 | thienyl | Benzyl |
| 55 | phenyl | Et |

Example 56

Using the general procedure shown for Example 50, the following compound may be synthesized from the corresponding cycloalkylamine.

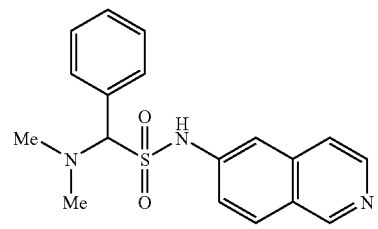 [SMILES: CN(C)C(c1ccccc1)S(=O)(=O)Nc1ccc2cnccc2c1]

Using largely the procedure set forth in Example 50 and substituting the appropriate starting materials, the compounds E57-E67 can be made.

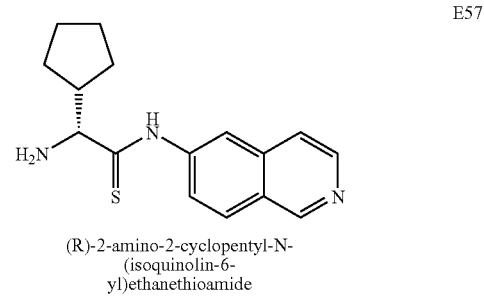

(R)-2-amino-2-cyclopentyl-N-(isoquinolin-6-yl)ethanethioamide

E57

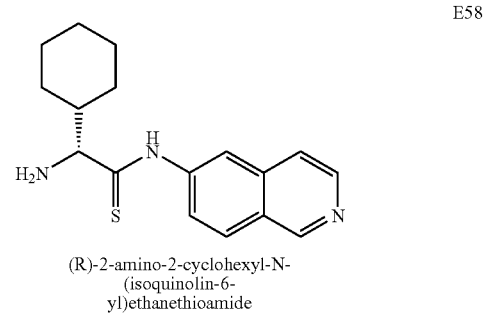

(R)-2-amino-2-cyclohexyl-N-(isoquinolin-6-yl)ethanethioamide

E58

-continued

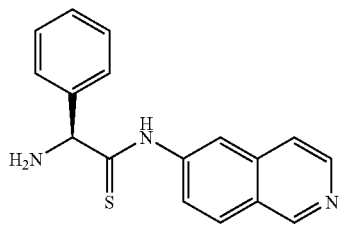

E59

(S)-2-amino-N-(isoquinolin-6-yl)-2-phenylethanethioamide

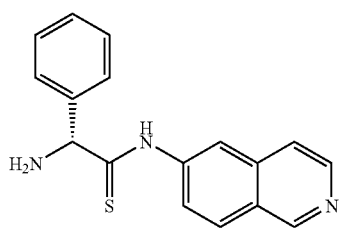

E60

(R)-2-amino-N-(isoquinolin-6-yl)-2-phenylethanethioamide

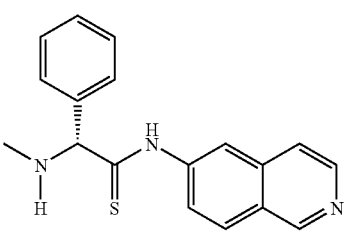

E61

(R)-N-(isoquinolin-6-yl)-2-(methylamino)-2-phenylethanethioamide

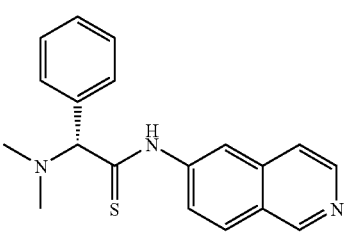

E62

(R)-2-(dimethylamino)-N-(isoquinolin-6-yl)-2-phenylethanethioamide

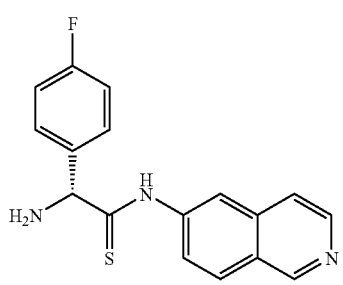

E63

(R)-2-amino-2-(4-fluorophenyl)-N-(isoquinolin-6-yl))ethanethioamide

-continued

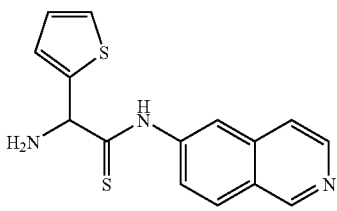

E64

2-amino-N-(isoquinolon-6-yl)-2-(thiophen-2-yl)ethanethioamide

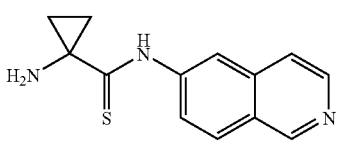

E65

1-amino-N-(isoquinolin-6-yl)cyclopropanecarbothioamide

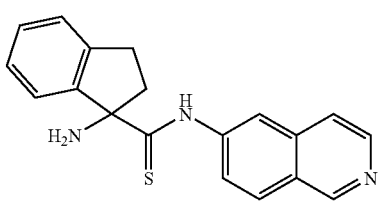

E66

1-amino-N-(isoquinolin-6-yl)-2,3-dihydro-1H-indene-1-carbothioamide

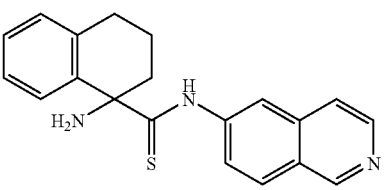

E67

1-amino-N-(isoquinolin-6-yl)-1,2,3,4-tetrahydronaphthalene-1-carbothioamide

Using largely the procedure set forth in Example 39 and substituting the appropriate starting materials, the compounds E68-E78 have been made.

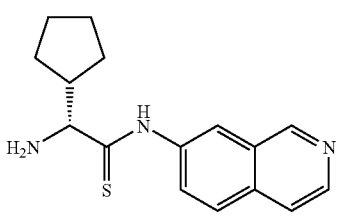

E68

(R)-2-amino-2-cyclopentyl-N-(isoquinolin-7-yl)acetamide

-continued

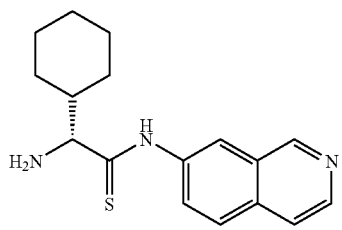

(R)-2-amino-2-cyclohexyl-N-(isoquinolin-7-yl)acetamide

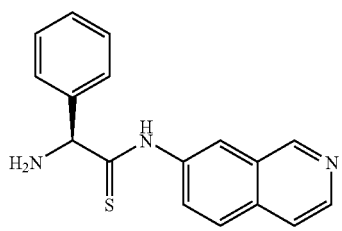

(S)-2-amino-N-(isoquinolin-7-yl)-2-phenylethanethioamide

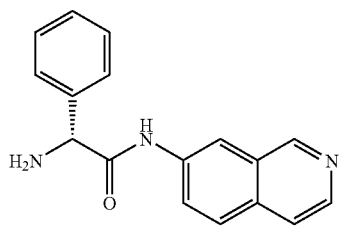

(R)-2-amino-N-(isoquinolin-7-yl)-2-phenylacetamide

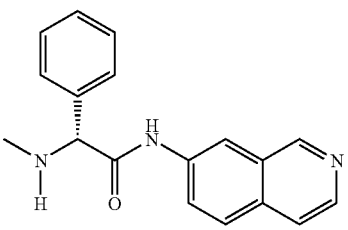

(R)-N-(isoquinolin-7-yl)-2-(methylamino)-2-phenylacetamide

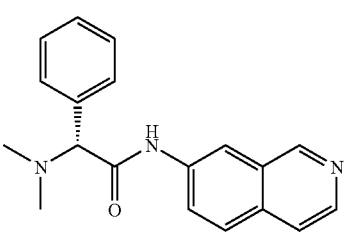

(R)-2-(dimethylamino)-N-(isoquinolin-7-yl)-2-phenylacetamide

-continued

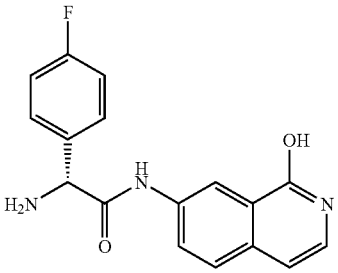

(R)-2-amino-2-(4-fluorophenyl)-N-(1-hydroxyisoquinolin-7-yl)acetamide

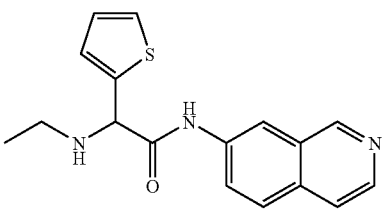

2-(ethylamino)-N-(isoquinolin-7-yl)-2-(thiophen-2-yl)acetamide

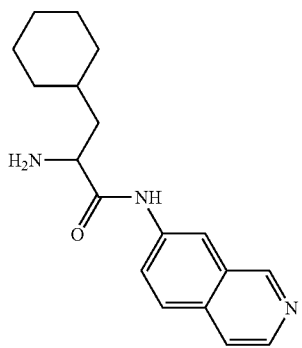

2-amino-3-cyclohexyl-N-(isoquinolin-7-yl)propanamide

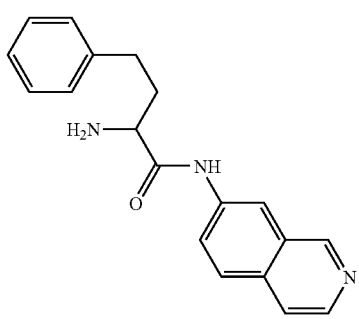

2-amino-N-(isoquinolin-7-yl)-4-phenylbutanamide

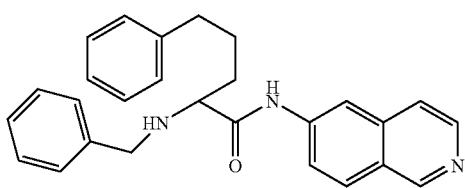

2-(benzylamino)-N-(isoquinolin-7-yl)-5-phenylpentanamide

Example 79

Preparation of (R)-2-(dimethylamino)-N-(1-hydroxyisoquinolin-6-yl)-2-(thiophen-3-yl)acetamide hydrochloride. (E79)

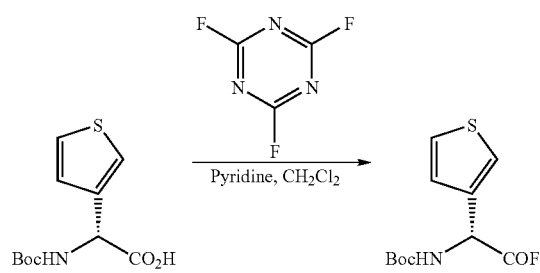

To (R)-2-(tert-butoxycarbonylamino)-2-(thiophen-3-yl) acetic acid in CH₂Cl₂ cooled to −10° C. was added pyridine and cyanuric fluoride. The solution was stirred for 1 hour at −10° C., quenched with ice and extracted with CH₂Cl₂ and ice cold water, dried (Na₂SO₄), filtered and evaporated to give (R)-tert-butyl 2-fluoro-2 oxo-1-(thiophen-3-yl)ethylcarbamate.

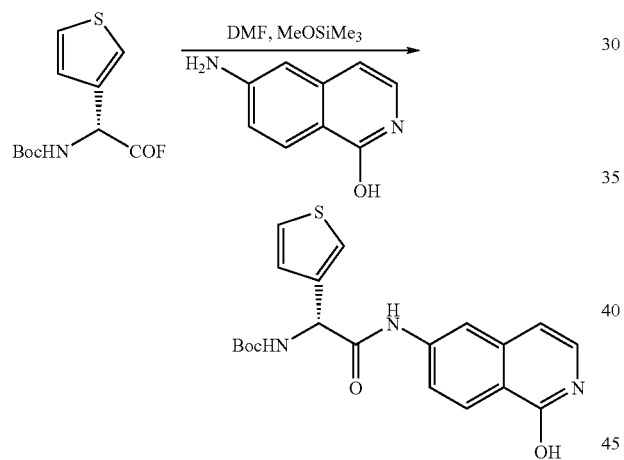

To 6-aminoisoquinolin-1-ol in DMF was added methoxytrimethylsilane and (R)-tert-butyl 2-fluoro-2 oxo-1-(thiophen-3-yl)ethylcarbamate and the solution was stirred at room temperature for 6 h. The mixture was poured into EtOAc, washed with NH₄Cl(sat)/HCl (1N) followed by NaHCO₃ (0.05%), dried (Na₂SO₄), filtered and evaporated. Column chromatography (SiO₂, 5% MeOH, CH₂Cl₂) gave pure (R)-tert-butyl 2-(1-hydroxyisoquinolin-6-ylamino)-2-oxo-1-(thiophen-3-yl)ethylcarbamate) (91.8% ee by Chiracel OD-RH).

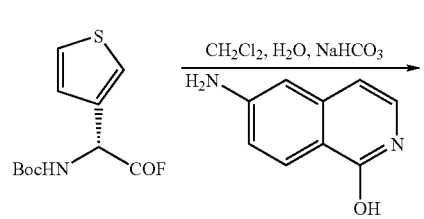

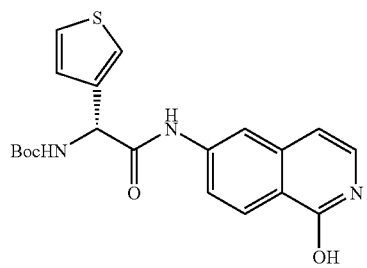

To 6-aminoisoquinolin-1-ol in H₂O was added NaHCO₃ followed by a solution of (R)-tert-butyl 2-fluoro-2 oxo-1-(thiophen-3-yl)ethylcarbamate in CH₂Cl₂. The solution was stirred for 4 hours, extracted with EtOAc and NH₄Cl(sat)/HCl (1N) and then with NaHCO₃ (0.05%), dried (Na₂SO₄), filtered and evaporated. Column chromatography (SiO₂, 5% MeOH, CH₂Cl₂) gave pure (R)-tert-butyl 2-(1-hydroxyisoquinolin-6-ylamino)-2-oxo-1-(thiophen-3-yl)ethylcarbamate (95% ee by Chiracel OD-RH)

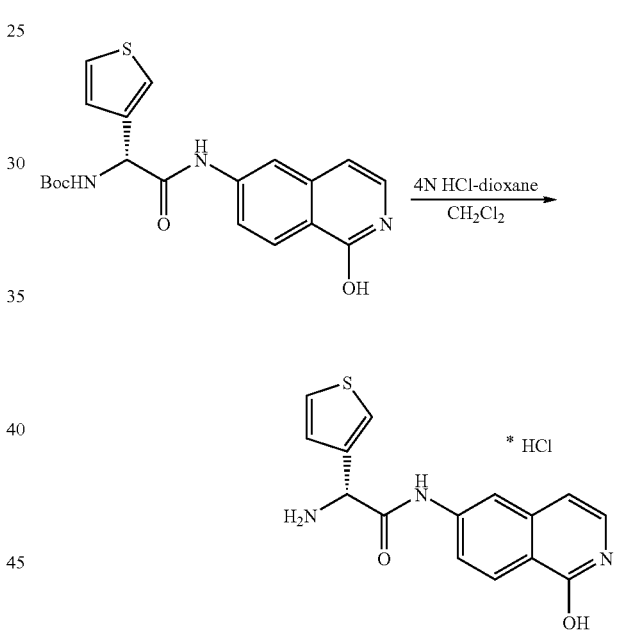

To (R)-tert-butyl-2-(1-hydroxyisoquinolin-6-ylamino)-2-oxo-1-(thiophen-3-yl)ethylcarbamate in CH₂Cl₂ was added 4N HCl-dioxane and solution was stirred at room temperature for 4 hours. The solvents were evaporated off to give pure (R)-2-amino-N-(1-hydroxyisoquinolin-6-yl)-2-thiophen-3-yl)acetamide hydrochloride

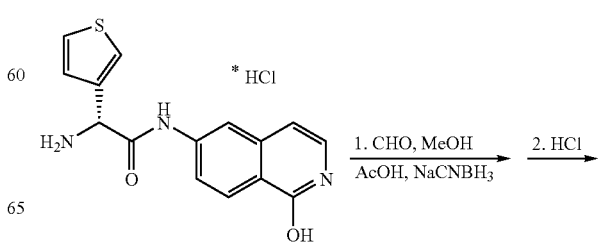

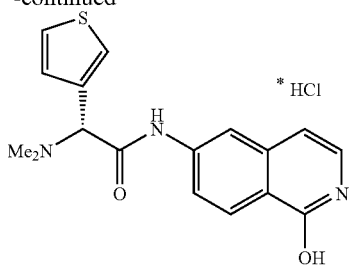

To (R)-2-amino-N-(1-hydroxyisoquinolin-6-yl)-2-thiophen-3-yl)acetamide hydrochloride in MeOH was added AcOH, CHO (37%) and NaCNBH₃ and the solution stirred for 30 minutes. The mixture was poured into NaHCO₃(sat) and extracted with CH₂Cl₂, dried (Na₂SO₄) filtered and evaporated. Column chromatography (SiO₂, 5% MeOH, CH₂Cl₂) gave pure (R)-2-(dimethylamino)-N-(1-hydroxyisoquinolin-6-yl)-2-(thiophen-3-yl)acetamide. The product was taken up in CH₂Cl₂, 4 N HCl was added and the solvents were evaporated to give (R)-2-(dimethylamino)-N-(1-hydroxyisoquinolin-6-yl)-2-(thiophen-3-yl)acetamide hydrochloride (E79).

Example 80

Preparation of (R)-2-(dimethylamino)-N-(isoquinolin-6-yl)-2-(thiophen-3-yl)acetamide hydrochloride. (E80)

Using largely the procedure set forth in Example 79 and substituting the appropriate starting materials, (R)-2-(dimethylamino)-N-(isoquinolin-6-yl)-2-(thiophen-3-yl)acetamide hydrochloride was made.

Example 81

Preparation of (R)-2-(methylamino)-N-(1-hydroxyisoquinolin-6-yl)-2-(thiophen-3-yl)acetamide hydrochloride. (E81)

Using largely the procedure set forth in Example 79 and substituting the appropriate starting materials, (R)-2-(methylamino)-N-(1-hydroxyisoquinolin-6-yl)-2-(thiophen-3-yl)acetamide hydrochloride was made.

Example 82

Preparation of (R)-2-(amino)-N-(isoquinolin-6-yl)-2-(thiophen-3-yl)acetamide hydrochloride. (E82)

Using largely the procedure set forth in Example 79 and substituting the appropriate starting materials, (R)-2-(amino)-N-(isoquinolin-6-yl)-2-(thiophen-3-yl)acetamide hydrochloride was made.

Example 83

Preparation of (R)-2-(methylamino)-N-(isoquinolin-6-yl)-2-(thiophen-3-yl)acetamide hydrochloride. (E83)

Using largely the procedure set forth in Example 79 and substituting the appropriate starting materials, (R)-2-(methylamino)-N-(isoquinolin-6-yl)-2-(thiophen-3-yl)acetamide hydrochloride was made.

Example 84

Preparation of (R)-2-(amino)-N-(isoquinolin-6-yl)-2-(thiophen-3-yl)acetamide hydrochloride. (E84)

Using largely the procedure set forth in Example 79 and substituting the appropriate starting materials, (R)-2-(amino)-N-(isoquinolin-6-yl)-2-(thiophen-3-yl)acetamide hydrochloride was made.

Example 85

Preparation of (R)-2-(amino)-N-(isoquinolin-6-yl)-2-(thiophen-3-yl)acetamide hydrochloride. (E85)

Using largely the procedure set forth in Example 79 and substituting the appropriate starting materials, variations of the compounds set forth in Examples 79-84 can be made in which the thiophene is substituted with a phenyl group.

Example 86

Using largely the procedure set forth in Example 79 and substituting the appropriate starting materials, substituted derivatives of the compounds in Examples 79-85 can be made. For example, the thiophene or phenyl group can be substituted with a halogen (such as fluorine or chlorine) or methyl groups.

Additionally, using largely the procedure set forth in Example 79 and substituting the appropriate starting materials, 3-thiophene derivatives of 2-thiophene derivatives of the compounds set forth in Examples 79-86 can be made.

Example 87

Preparation of (S)-tert-butyl 1-(isoquinolin-7-ylamino)-4-methyl-1-oxopentan-2-yl(methyl)carbamate (E86)

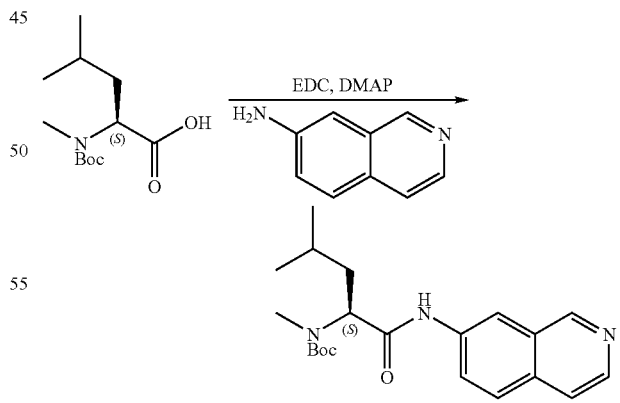

To (S)-2-(tert-butoxycarbonyl(methyl)amino)-4-methylpentanoic acid in DMF was added EDC, DMAP and isoquinolin-7-amine. This mixture was stirred for 4 hours and the reaction was washed with NaHCO₃ (sat), extracted with EtOAc, dried (Na₂SO₄), filtered and evaporated. Column chromatography (SiO$_2$, Hexanes/EtOAc) gave pure (S)-tert-butyl 1-(isoquinolin-7-ylamino)-4-methyl-1-oxopentan-2-yl(methyl)carbamate (E87).

Example 88

Preparation of (S)-N-(isoquinolin-7-yl)-4-methyl-2-(methylamino)pentanamide (E88)

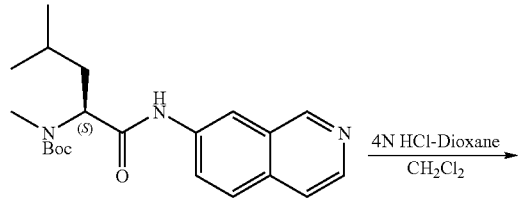

To (R)-tert-butyl-2-(1-hydroxyisoquinolin-6-ylamino)-2-oxo-1 phenyl-ethylcarbamate (E1) in CH$_2$Cl$_2$ was added HCl (4M in dioxane) and the solution was stirred overnight at room temperature. The reaction was concentrated to give (S)-N-(isoquinolin-7-yl)-4-methyl-2-(methylamino)pentanamide dihydrochloride (E88).

Example 89

Using largely the procedures set forth in Example 87 and 88 and substituting the appropriate starting materials, the compounds below can be made.

(S)-N-(isoquinolin-7-yl)-4-methyl-2-(methylamino)pentanamide (R)-N-(isoquinolin-7-yl)-4-methyl-2-(methylamino)pentanamide 2-(2,3-dichloro-4-(thiophene-2-carbonyl)phenoxy)-N-(isoquinolin-7-yl)acetamide N-(isoquinolin-7-yl)-2-(2-methyl-4-(thiophene-2-carbony)phenoxy)acetamide (R)-2-amino-N-(isoquinolin-7-yl)-2-(thiophen-2-yl)acetamide (S)-2-amino-N-(isoquinolin-7-yl)-2-(thiophen-2-yl)acetamide N-(isoquinolin-7-yl)piperidine-3-carboxamide (1s,4s)-4-amino-N-(isoquinolin-7-yl)cyclohexanecarboxamide N-(isoquinolin-7-yl)piperidine-4-carboxamide

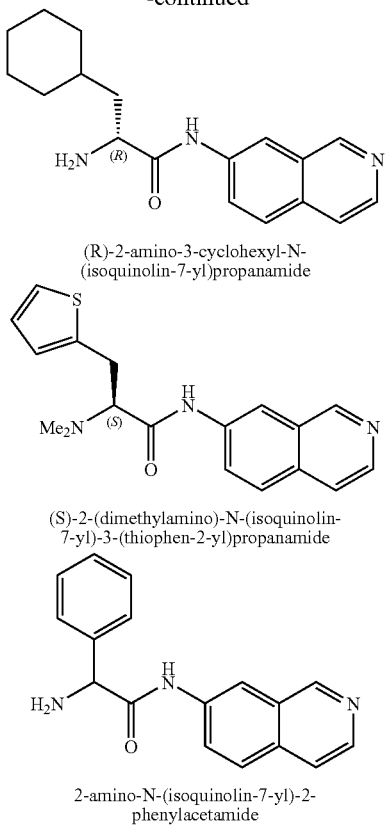

(R)-2-amino-3-cyclohexyl-N-(isoquinolin-7-yl)propanamide (S)-2-(dimethylamino)-N-(isoquinolin-7-yl)-3-(thiophen-2-yl)propanamide 2-amino-N-(isoquinolin-7-yl)-2-phenylacetamide Reference Example Two Pharmacological Activity for Glaucoma Assay Pharmacological activity for glaucoma can be demonstrated using assays designed to test the ability of the subject compounds to decrease intraocular pressure. Examples of such assays are described in the following reference, incorporated herein by reference: C. Liljebris, G. Selen, B. Resul, J. Sternschantz, and U. Hacksell, "Derivatives of 17-phenyl-18,19,20-trinorprostaglandin $F_{2\alpha}$ Ispropyl Ester: Potential Anti-glaucoma Agents", *Journal of Medicinal Chemistry*, Vol. 38 (2) 1995, pp. 289-304.

Example 90

Topical pharmaceutical compositions for lowering intraocular pressure are prepared by conventional methods and formulated as follows:

| Ingredient | Amount (wt %) |
| --- | --- |
| 6-aminoisoquinoline Derivative or 7-aminoisoquinoline Derivative | 0.50 |
| Dextran 70 | 0.1 |
| Hydroxypropyl methylcellulose | 0.3 |
| Sodium Chloride | 0.77 |
| Potassium chloride | 0.12 |
| Disodium EDTA | 0.05 |
| Benzalkonium chloride | 0.01 |
| HCl and/or NaOH | pH 7.0-7.2 |
| Purified water | q.s. to 100% |

A compound according to this invention is used as the 6- or 7-aminoisoquinoline derivative. When the composition is topically administered to the eyes once or more daily as 40 microliter drops, the above composition decreases intraocular pressure in a patient suffering from glaucoma.

Example 91

A pharmaceutical composition is prepared according to Example 90, where the 6-aminoisoquinoline derivative is (R)-2-amino-N-(isoquinolin-6-yl)-2-phenylacetamide dihydrochloride (E2). When topically administered to the eyes as a drop 4 times per day, the composition substantially decreases intraocular pressure and serves as a neuroprotective agent.

Example 92

A pharmaceutical composition is prepared according to Example 90, where the 6-aminoisoquinoline derivative is (R)-2-(dimethylamino)-N-(isoquinolin-6-yl)-2-phenylacetamide dihydrochloride (E3). When topically administered to the eyes as a drop twice per day, the composition substantially decreases intraocular pressure.

Example 93

When the pharmaceutical composition of Example 91 is topically administered to the eyes as a drop twice per day, the composition substantially decreases allergic symptoms and relieves dry eye syndrome.

Example 94

Example 90 is repeated using (S)-2-(dimethylamino)-N-(isoquinolin-6-yl)-2-phenylacetamide dihydrochloride (E3) according to this invention. When administered as a drop as needed, the above composition substantially decreases hyperemia, redness and ocular irritation.

Example 95

A pharmaceutical composition is prepared according to Example 90, where the 6-aminoisoquinoline derivative is (R)-N-(isoquinolin-6-yl amino)-2-(methylamino)-2-o-fluorophenyl acetamide dihydrochloride (E17). When topically administered to the eyes as a drop 4 times per day, the composition substantially decreases intraocular pressure and serves as a neuroprotective agent.

Example 96

A pharmaceutical composition is prepared according to Example 90, where the 6-aminoisoquinoline derivative is (R)-N-(isoquinolin-6-ylamino)-2-(ethylamino)-2-p-methylphenyl acetamide dihydrochloride (E18). When topically administered to the eyes as a drop twice per day, the composition substantially decreases intraocular pressure.

Example 97

A pharmaceutical composition is prepared according to Example 90, where the 6-aminoisoquinoline derivative is N-(isoquinolin-6-yl)cyclohexylamino phenylmethanesulfonamide (E50). When topically administered to the eyes as a drop twice per day, the composition substantially decreases allergic symptoms and relieves dry eye syndrome.

Example 98

A pharmaceutical composition is prepared according to Example 90, where the 6-aminoisoquinoline derivative is (R)-N-(isoquinolin-6-ylamino)-2-amino-2-cyclohexyl acetamide dihydrochloride (E9). When topically administered to the eyes as a drop as needed, the composition substantially decreases allergic symptoms

Example 99

A pharmaceutical composition is prepared according to Example 90, where the 6-aminoisoquinoline derivative is (R)-N-(isoquinolin-6-yl)-2-phenyl-2-(piperazin-1-yl)acetamide (E40). When topically administered to the eyes as a drop as needed, the composition substantially decreases hyperemia, redness and ocular irritation.

Example 100

A pharmaceutical composition is prepared according to Example 90, where the 6-aminoisoquinoline derivative is (R)-N-(isoquinolin-6-yl)-2-phenyl-2-(tetrahydropyrimidin-1(2H)-yl)acetamide (E41). When topically administered to the eyes as a drop twice a day or as needed, the composition substantially decreases intraocular pressure.

Example 101

A pharmaceutical composition is prepared according to Example 90, where the 6-aminoisoquinoline derivative is (S)-2-cyclohexyl-N-(isoquinolin-6-yl)-2-(propylamino)acetamide (E25). When topically administered to the eyes as a drop twice a day or as needed, the composition substantially decreases intraocular pressure.

Example 102

A pharmaceutical composition is prepared according to Example 90, where the 7-aminoisoquinoline derivative is (S)-tert-butyl 1-(isoquinolin-7-ylamino)-4-methyl-1-oxo-pentan-2-yl(methyl)carbamate (E87). When topically administered to the eyes as a drop 4 times per day, the composition substantially decreases intraocular pressure.

Example 103

A pharmaceutical composition is prepared according to Example 90, where the 7-aminoisoquinoline derivative is (S)-N-(isoquinolin-7-yl)-4-methyl-2-(methylamino)pentanamide dihydrochloride (E88). When topically administered to the eyes as a drop 4 times per day, the composition substantially decreases intraocular pressure.

Example 104

A pharmaceutical composition is prepared according to Example 79, where the 7-aminoisoquinoline derivative is one selected from Example 89. When topically administered to the eyes as a drop 4 times per day, the composition substantially decreases intraocular pressure.

Example 105

Topical Pharmaceutical Compositions for Lowering intraocular pressure are prepared by conventional methods and formulated as follows:

| Ingredient | Amount (wt %) |
| --- | --- |
| 6-aminoisoquinoline Derivative or 7-aminoisoquinoline Derivative | 0.30 |
| Methyl Cellulose | 2.0 |
| Benzalkonium chloride | 0.01 |
| Phosphate Buffered Saline | q.s. to 100% |

A compound according to this invention is used as the 6- or 7-aminoisoquinoline derivative. When the composition is topically administered to the eyes once or more daily as 40 microliter drops, the above composition decreases intraocular pressure in a patient suffering from glaucoma.

Example 106

A pharmaceutical composition was prepared according to Example 105, where the 6-aminoisoquinoline derivative was (R)-2-(dimethylamino)-N-(1-hydroxyisoquinolin-6-yl)-2-(thiophen-3-yl)acetamide hydrochloride (E79). When a 40 microliter drop was topically administered to the eyes of a Dutch-belted rabbit once daily, the composition substantially decreased intraocular pressure. In some tests, the intraocular pressure was decreased by greater than 5 mm of mercury.

Example 107

A pharmaceutical composition was prepared according to Example 105, where the 6-aminoisoquinoline derivative was (R)-2-(dimethylamino)-N-(isoquinolin-6-yl)-2-(thiophen-3-yl)acetamide hydrochloride (E80). When a 40 microliter drop was topically administered to the eyes of a Dutch-belted rabbit once daily, the composition substantially decreased intraocular pressure. In some tests, the intraocular pressure was decreased by greater than 5 mm of mercury.

Example 108

Pharmaceutical compositions were prepared according to Example 105, where the 6-aminoisoquinoline derivative was each of Examples 81-84. When a 40 microliter drop was topically administered to the eyes of a Dutch-belted rabbit once daily, the composition substantially decreased intraocular pressure. In some tests, the intraocular pressure was decreased by greater than 5 mm of mercury.

Example 109

A pharmaceutical composition is prepared according to Example 105, where the 6-aminoisoquinoline derivatives are those set forth in Examples 85 and 86. When a 40 microliter drop is topically administered to the eyes of a Dutch-belted rabbit once daily, the composition substantially decreases intraocular pressure.

While the invention has been described in detail and with reference to specific embodiments thereof, it will be apparent to one skilled in the art that various changes and modifications can be made without departing from the spirit and scope of the invention.

What is claimed is:

1. A compound according to Formula (I):

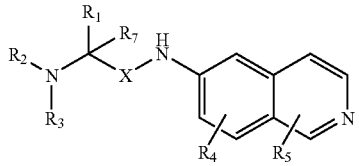

any optical isomer, diastereomer, or enantiomer of Formula I or a physiologically acceptable salt or solvate thereof,
wherein $R_1$ is an aryl group, a heteroaryl group, a cycloalkyl group, a heterocycloalkyl group,
$R_7$ is hydrogen, $C_1$-$C_4$ alkyl, cyano, or $R_1$ and $R_7$ combine to form a ring of at least three and at most eight member atoms,
$R_2$, and $R_3$ are, independently, hydrogen, hydroxyl, halogen, $C_1$-$C_4$ alkyl, $C_2$-$C_4$ alkenyl, $C_2$-$C_4$ alkynyl, amino, nitro, cyano, $C_1$-$C_4$ carbonyl, $C_1$-$C_4$ carbonylamino, $C_1$-$C_4$ alkoxy, $C_1$-$C_4$ sulfonyl, $C_1$-$C_4$ sulfonylamino, $C_1$-$C_4$ thioalkyl, $C_1$-$C_4$ carboxyl, cycloalkyl, heterocycloalkyl, aryl, $C_1$-$C_4$ alkyl aryl, heteroaryl, or $C_1$-$C_4$ alkyl heteroaryl; or $R_2$ and $R_3$ combine to form a ring of at least five and at most eight member atoms,
X is a carbonyl group, a sulfone group, thiocarbonyl or methylene, and
$R_4$ and $R_5$ are independently, halogen, hydrogen, hydroxy, alkyl, alkoxy, amino, carbonyl, cycloalkyl, heterocycloalkyl, aryl, $C_1$-$C_4$ alkyl aryl, heteroaryl, $C_1$-$C_4$ alkyl heteroaryl, alkenyl, alkynyl, nitro, cyano, $C_1$-$C_4$ carbonylamino, $C_1$-$C_4$ sulfonyl, $C_1$-$C_4$ sulfonylamino, $C_1$-$C_4$ thioalkyl or $C_1$-$C_4$ carboxyl.

2. The compound of claim 1, wherein X is a carbonyl group, $R_1$ is a substituted or unsubstituted phenyl ring, and $R_7$ is hydrogen.

3. The compound of claim 2, wherein the compound is a single enantiomer.

4. The compound of claim 2, wherein $R_4$ and $R_5$ are each hydrogen.

5. The compound of claim 2, wherein $R_2$ is hydrogen.

6. The compound of claim 1, wherein X is a carbonyl group, $R_1$ is an aryl group and $R_7$ is a methyl group.

7. The compound of claim 1, wherein X is a carbonyl group, and $R_1$ and $R_7$ combine to form a ring of at least three and at most 8 member atoms.

8. The compound of claim 1, wherein X is a sulfone group, and $R_4$ and $R_5$ are independently, a halogen, hydrogen, hydroxyl, or alkyl.

9. The compound of claim 1, wherein X is a sulfone group, and $R_1$ and $R_7$ combine to form a ring of at least three and at most 8 member atoms.

10. The compound of claim 1, wherein X is a carbonyl group, $R_1$ is an aryl group, and $R_4$ and $R_5$ are each hydrogen.

11. The compound of claim 1, wherein X is a carbonyl group, $R_1$ is a cycloalkyl group, $R_2$ and $R_3$ are each methyl, and $R_5$ is hydroxy.

12. The compound of claim 1, wherein X is a carbonyl group or a sulfone group, $R_4$ and $R_5$ are each hydrogen, and $R_7$ is $C_1$ alkyl.

13. The compound of claim 1, wherein X is a carbonyl group or a sulfone group and $R_1$ is a para-substituted aryl group.

14. The compound of claim 1, wherein X is a carbonyl group or a sulfone group, and $R_2$ is $C_1$-$C_4$ alkyl.

15. The compound of claim 1, wherein X is a sulfone group, and $R_2$ and $R_3$ combine to form a ring of at least five and at most eight member atoms.

16. The compound of claim 1, wherein X is a carbonyl group, $R_1$ is an aryl group, a heteroaryl group or a cycloalkyl group, $R_7$ is hydrogen or $C_1$ alkyl, $R_2$ and $R_3$ are, independently, hydrogen, $C_1$-$C_4$ alkyl, $C_1$-$C_4$ alkyl aryl, or $R_2$ and $R_3$ combine to form a ring of at least five and at most eight member atoms, and $R_4$ and $R_5$ are each hydrogen.

17. The compound of claim 1, wherein X is a sulfone group, $R_1$ is an aryl group, or $R_1$ and $R_7$ combine to form a ring of at least three and at most eight member atoms, $R_2$ and $R_3$ are, independently, hydrogen, an aryl group, $C_1$-$C_4$ alkyl, or a cycloalkyl group, and $R_4$ and $R_5$ are each hydrogen.

18. The compound of claim 1, wherein X is a thiocarbonyl group, $R_1$ is an aryl group, a heteroaryl group, a cycloalkyl group, or $R_1$ and $R_7$ combine to form a ring of at least three and at most eight member atoms, $R_2$ and $R_3$ are, independently, hydrogen, or $C_1$-$C_4$ alkyl, and $R_4$ and $R_5$ are each hydrogen.

19. The compound of claim 1, wherein X is a carbonyl group, $R_1$ is a substituted or unsubstituted thiophenyl ring, and $R_7$ is hydrogen.

20. The compound of claim 1, wherein X is a carbonyl group, $R_1$ is a substituted or unsubstituted thiophenyl or phenyl ring, $R_7$ is hydrogen, $R_2$ and $R_3$ are, independently, hydrogen, or $C_1$-$C_4$ alkyl.

21. The compound of claim 20, wherein $R_1$ is thiophenyl.

22. The compound of claim 21, wherein one of $R_4$ and $R_5$ is hydroxy.

23. The compound of claim 21, wherein $R_4$ and $R_5$ are each hydrogen.

24. The compound of claim 20, wherein $R_1$ is phenyl.

25. The compound of claim 24, wherein one of $R_4$ and $R_5$ is hydroxy.

26. The compound of claim 24, wherein $R_4$ and $R_5$ are each hydrogen.

27. The compound of claim 1, wherein the compound is (R)-2-(dimethylamino)-N-(1-hydroxyisoquinolin-6-yl)-2-(thiophen-3-yl)acetamide.

28. The compound of claim 1, wherein the compound is (R)-2-(dimethylamino)-N-(1-isoquinolin-6-yl)-2-(thiophen-3-yl)acetamide.

29. A compound selected from the following:

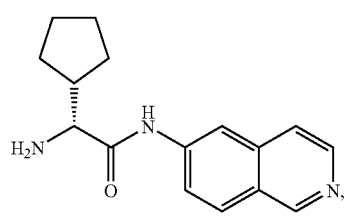

(R)-2-amino-2-cyclopentyl-N-
(isoquinolin-6-yl)acetamide

-continued (R)-2-amino-2-cyclohexyl-N-(isoquinolin-6-yl)acetamide (S)-2-amino-N-(isoquinolin-6-yl)-2-phenylacetamide (R)-2-amino-N-(isoquinolin-6-yl)-2-phenylacetamide (R)-N-(isoquinolin-6-yl)-2-(methylamino)-2-phenylacetamide (R)-2-(dimethylamino)-N-(isoquinolin-6-yl)-2-phenylacetamide (R)-2-amino-2-(4-fluorophenyl)-N-(isoquinolin-6-yl)acetamide -continued 2-amino-N-(isoquinolin-6-yl)-2-(thiophen-2-yl)acetamide 1-amino-N-(isoquinolin-6-yl)cyclopropanecarboxamide 1-amino-N-(isoquinolin-6-yl)-2,3-dihydro-1H-indene-1-carboxamide or 1-amino-N-(isoquinolin-6-yl)-1,2,3,4-tetrahydronaphthalene-1-carboxamide.

30. A 7-aminoisoquinoline compound according to Formula (II)

any optical isomer, diastereomer, or enantiomer of Formula II or a physiologically acceptable salt or solvate thereof, wherein $R_1$ is hydrogen, a lower alkyl group, an aryl group, a heteroaryl group, a cycloalkyl group, a heterocycloalkyl group, $R_7$ is $C_1$-$C_6$ alkyl, $C_2$-$C_6$ alkenyl, $C_2$-$C_6$ alkynyl, cyano, aryl group, heteroaryl group, alkyl aryl group, cycloalkyl group or heterocycloalkyl group or $R_1$ and $R_7$ combine to form a ring, of at least three and at most 8 member atoms, $R_2$, and $R_3$ are, independently, hydrogen, hydroxyl, unsubstituted $C_1$-$C_4$ alkyl, $C_2$-$C_4$ alkenyl, $C_2$-$C_4$ alkynyl, amino, cyano, unsubstituted $C_1$-$C_4$ carbonyl, or $C_1$-$C_4$ carboxyl, aryl group, heteroaryl group, unsubstituted alkyl aryl group, cycloalkyl group or heterocycloalkyl group; or $R_2$ and $R_3$ combine to form a ring of at least five and at most 8 member atoms, X is a carbonyl group, a sulfone group, thiocarbonyl or methylene, $R_4$ is halogen, hydrogen, hydroxy, alkyl, alkoxy, carbonyl, cycloalkyl, heterocycloalkyl, aryl, $C_1$-$C_4$ alkyl aryl, heteroaryl, $C_1$-$C_4$ alkyl heteroaryl, and $R_5$ is halogen, hydrogen, hydroxy, alkyl, alkoxy, carbonyl, cycloalkyl, heterocycloalkyl, aryl, $C_1$-$C_4$ alkyl aryl, heteroaryl, $C_1$-$C_4$ alkyl heteroaryl.

31. The compound of claim 30, wherein $R_3$ is $C_1$-$C_4$ alkyl.

32. The compound of claim 30, wherein $R_1$ is hydrogen and $R_7$ is an aryl group, a heteroaryl group, an alkyl aryl group or a cycloalkyl group.

33. The compound of claim 30, wherein $R_1$ is hydrogen, $R_2$ and $R_3$ are each, independently hydrogen, $C_1$-$C_4$ alkyl, or alkyl aryl group, $R_4$ and $R_5$ are each hydrogen, and $R_7$ is an aryl group, a heteroaryl group, an alkyl aryl group or a cycloalkyl group.

34. A pharmaceutical composition comprising
a) a 6-aminoisoquinoline derivative according to Formula I

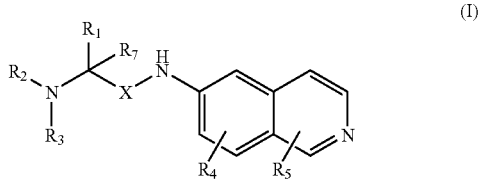

(I)

any optical isomer, diastereomer, or enantiomer of Formula I or a physiologically acceptable salt or solvate thereof, wherein $R_1$ is an aryl group, a heteroaryl group, a cycloalkyl group, a heterocycloalkyl group, $R_7$ is hydrogen, $C_1$-$C_4$ alkyl, cyano, or $R_1$ and $R_7$ combine to form a ring of at least three and at most eight member atoms, $R_2$, and $R_3$ are, independently, hydrogen, hydroxyl, halogen, $C_1$-$C_4$ alkyl, $C_2$-$C_4$ alkenyl, $C_2$-$C_4$ alkynyl, amino, nitro, cyano, $C_1$-$C_4$ carbonyl, $C_1$-$C_4$ carbonylamino, $C_1$-$C_4$ alkoxy, $C_1$-$C_4$ sulfonyl, $C_1$-$C_4$ sulfonylamino, $C_1$-$C_4$ thioalkyl, $C_1$-$C_4$ carboxyl, cycloalkyl, heterocycloalkyl, aryl, $C_1$-$C_4$ alkyl aryl, heteroaryl, or $C_1$-$C_4$ alkyl heteroaryl; or $R_2$ and $R_3$ combine to form a ring of at least five and at most eight member atoms, X is a carbonyl group, a sulfone group, thiocarbonyl or methylene, and $R_4$ and $R_5$ are independently, halogen, hydrogen, hydroxy, alkyl, alkoxy, amino, carbonyl, cycloalkyl, heterocycloalkyl, aryl, $C_1$-$C_4$ alkyl aryl, heteroaryl, $C_1$-$C_4$ alkyl heteroaryl, alkenyl, alkynyl, nitro, cyano, $C_1$-$C_4$ carbonylamino, $C_1$-$C_4$ sulfonyl, $C_1$-$C_4$ sulfonylamino, $C_1$-$C_4$ thioalkyl or $C_1$-$C_4$ carboxyl, or
a 7-isoquinoline derivative according to Formula II

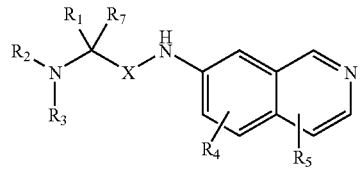

any optical isomer, diastereomer, or enantiomer of Formula II or a physiologically acceptable salt or solvate thereof, wherein $R_1$ is hydrogen, a lower alkyl group, an aryl group, a heteroaryl group, a cycloalkyl group, a heterocycloalkyl group, $R_7$ is $C_1$-$C_6$ alkyl, $C_2$-$C_6$ alkenyl, $C_2$-$C_6$ alkynyl, cyano, aryl group, heteroaryl group, alkyl aryl group, cycloalkyl group or heterocycloalkyl group or $R_1$ and $R_7$ combine to form a ring, of at least three and at most 8 member atoms, $R_2$, and $R_3$ are, independently, hydrogen, hydroxyl, unsubstituted $C_1$-$C_4$ alkyl, $C_2$-$C_4$ alkenyl, $C_2$-$C_4$ alkynyl, amino, nitro, cyano, unsubstituted $C_1$-$C_4$ carbonyl, or $C_1$-$C_4$ carboxyl, aryl group, heteroaryl group, unsubstituted alkyl aryl group, cycloalkyl group or heterocycloalkyl group; or $R_2$ and $R_3$ combine to form a ring of at least five and at most 8 member atoms, X is a carbonyl group, a sulfone group, thiocarbonyl or methylene, $R_4$ is halogen, hydrogen, hydroxy, alkyl, alkoxy, carbonyl, cycloalkyl, heterocycloalkyl, aryl, $C_1$-$C_4$ alkyl aryl, heteroaryl, $C_1$-$C_4$ alkyl heteroaryl, and $R_5$ is halogen, hydrogen, hydroxy, alkyl, alkoxy, carbonyl, cycloalkyl, heterocycloalkyl, aryl, $C_1$-$C_4$ alkyl aryl, heteroaryl, $C_1$-$C_4$ alkyl heteroaryl, and b) a carrier.

35. The composition of claim 34, wherein the carrier is a systemic carrier.

36. The composition of claim 35, wherein the composition comprises about 0.001% to about 10% of the 6- or 7-aminoisoquinoline derivative and about 90 to about 99.99% of the carrier.

37. The composition of claim 35, wherein the composition comprises about 25% to about 50% of the 6- or 7-aminoisoquinoline derivative and about 50 to about 75% of the carrier.

38. The composition of claim 35, wherein the carrier comprises at least one of a) diluents, b) lubricants, c) binders, d) disintegrants, e) colorants, f) flavors, g) sweeteners, h) antioxidants, j) preservatives, k) glidants, m) solvents, n) suspending agents, o) wetting agents, p) surfactants, or combinations thereof.

39. The composition of claim 34, wherein the carrier is a topical carrier.

40. The composition of claim 39, wherein the composition comprises about 0.001% to about 0.3% of the 6- or 7-aminoisoquinoline derivative when the $IC_{50}$ is 1 nM, about 0.01% to about 1% of the 6- or 7-aminoisoquinoline derivative when the $IC_{50}$ is 10 nM, about 0.1% to about 10% of the 6- or 7-aminoisoquinoline derivative when the $IC_{50}$ is 100 nM, and about 1% to about 100% of the 6- or 7-aminoisoquinoline derivative when the $IC_{50}$ is 1000 nM.

41. The composition of claim 39, wherein the carrier comprises water and at least one of a sugar, a sugar alcohol, cellulose or derivatives thereof, salt, disodium EDTA and a pH adjusting additive.

42. The composition of claim 34, wherein the derivative is (R)-2-(dimethylamino)-N-(1-hydroxyisoquinolin-6-yl)-2-(thiophen-3-yl)acetamide.

43. The composition of claim 34, wherein the derivative is (R)-2-(dimethylamino)-N-(1-isoquinolin-6-yl)-2-(thiophen-3-yl)acetamide.

44. A method for treating a disease in a mammal comprising:
administering to a mammal a safe and effective amount of a 6-aminoisoquinoline derivative according to Formula I

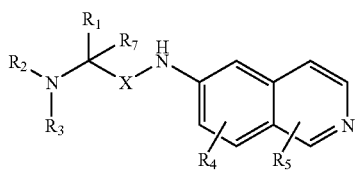
(I)

any optical isomer, diastereomer, or enantiomer of Formula I or a physiologically acceptable salt or solvate thereof, wherein $R_1$ is an aryl group, a heteroaryl group, a cycloalkyl group, a heterocycloalkyl group, the stereocenter being either 'R' or 'S' in configuration, $R_7$ is hydrogen, $C_1$-$C_4$ alkyl, cyano, or $R_1$ and $R_7$ combine to form a ring of at least three and at most eight member atoms, $R_2$, and $R_3$ are, independently, hydrogen, hydroxyl, halogen, $C_1$-$C_4$ alkyl, $C_2$-$C_4$ alkenyl, $C_2$-$C_4$ alkynyl, amino, nitro, cyano, $C_1$-$C_4$ carbonyl, $C_1$-$C_4$ carbonylamino, $C_1$-$C_4$ alkoxy, $C_1$-$C_4$ sulfonyl, $C_1$-$C_4$ sulfonylamino, $C_1$-$C_4$ thioalkyl, $C_1$-$C_4$ carboxyl, cycloalkyl, heterocycloalkyl, aryl, $C_1$-$C_4$ alkyl aryl, heteroaryl, or $C_1$-$C_4$ alkyl heteroaryl; or $R_2$ and $R_3$ combine to form a ring of at least five and at most eight member atoms, X is a carbonyl group, a sulfone group, thiocarbonyl or methylene, and $R_4$ and $R_5$ are independently, halogen, hydrogen, hydroxy, alkyl, alkoxy, amino, carbonyl, cycloalkyl, heterocycloalkyl, aryl, $C_1$-$C_4$ alkyl aryl, heteroaryl, $C_1$-$C_4$ alkyl heteroaryl, alkenyl, alkynyl, nitro, cyano, $C_1$-$C_4$ carbonylamino, $C_1$-$C_4$ sulfonyl, $C_1$-$C_4$ sulfonylamino, $C_1$-$C_4$ thioalkyl or $C_1$-$C_4$ carboxyl, wherein the disease is glaucoma or a neurodegenerative eye disease.

45. The method according to claim 44, wherein $R_1$ is an aryl group, a heteroaryl group, or a cycloalkyl group, $R_2$, and $R_3$ are, independently, hydrogen, hydroxyl, halogen, $C_1$-$C_4$ alkyl, $C_2$-$C_4$ alkenyl, $C_2$-$C_4$ alkynyl, amino, nitro, cyano, $C_1$-$C_4$ carbonyl, $C_1$-$C_4$ carbonylamino, $C_1$-$C_4$ alkoxy, $C_1$-$C_4$ sulfonyl, $C_1$-$C_4$ sulfonylamino, $C_1$-$C_4$ thioalkyl or $C_1$-$C_4$ carboxyl, and $R_4$ and $R_5$ are each hydrogen.

46. The method of claim 44, wherein the derivative is (R)-2-(dimethylamino)-N-(1-hydroxyisoquinolin-6-yl)-2-(thiophen-3-yl)acetamide.

47. The method of claim 44, wherein the derivative is (R)-2-(dimethylamino)-N-(1-isoquinolin-6-yl)-2-(thiophen-3-yl)acetamide.

48. A method for treating a disease in a mammal comprising:

administering to a mammal a safe and effective amount of 7-isoquinoline derivative according to Formula II

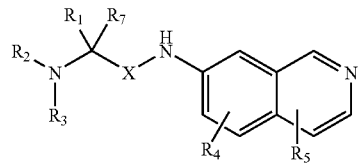

any optical isomer, diastereomer, or enantiomer of Formula II or a physiologically acceptable salt or solvate thereof, wherein $R_1$ is hydrogen, a lower alkyl group, an aryl group, a heteroaryl group, a cycloalkyl group, a heterocycloalkyl group, the stereocenter being either 'R' or 'S' in configuration, $R_7$ is $C_1$-$C_6$ alkyl, $C_2$-$C_6$ alkenyl, $C_2$-$C_6$ alkynyl, cyano, aryl group, heteroaryl group, alkyl aryl group, cycloalkyl group or heterocycloalkyl group or $R_1$ and $R_7$ combine to form a ring, of at least three and at most 8 member atoms, $R_2$, and $R_3$ are, independently, hydrogen, hydroxyl, halogen, $C_1$-$C_4$ alkyl, $C_2$-$C_4$ alkenyl, $C_2$-$C_4$ alkynyl, amino, nitro, cyano, $C_1$-$C_4$ carbonyl, $C_1$-$C_4$ carbonylamino, $C_1$-$C_4$ alkoxy, $C_1$-$C_4$ sulfonyl, $C_1$-$C_4$ sulfonylamino, $C_1$-$C_4$ thioalkyl or $C_1$-$C_4$ carboxyl, aryl group, heteroaryl group, alkyl aryl group, cycloalkyl group or heterocycloalkyl group; or $R_2$ and $R_3$ combine to form a ring of at least five and at most 8 member atoms, X is a carbonyl group, a sulfone group, thiocarbonyl or methylene, and $R_4$ and $R_5$ are independently, halogen, hydrogen, hydroxy, alkyl, alkoxy, amino, carbonyl, cycloalkyl, heterocycloalkyl, aryl, $C_1$-$C_4$ alkyl aryl, heteroaryl, $C_1$-$C_4$ alkyl heteroaryl, wherein the disease is glaucoma or a neurodegenerative eye disease.

* * * * *